United States Patent
Reinhardt et al.

(10) Patent No.: US 6,872,180 B2
(45) Date of Patent: Mar. 29, 2005

(54) DEVICE AND PROCESS FOR QUANTIFYING BODIES BY MEANS OF ULTRASOUND

(75) Inventors: Michael Reinhardt, Berlin (DE); Peter Hauff, Berlin (DE); Andreas Briel, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/400,928

(22) Filed: Mar. 28, 2003

(65) Prior Publication Data

US 2004/0092820 A1 May 13, 2004

Related U.S. Application Data

(60) Provisional application No. 60/378,358, filed on May 8, 2002.

(30) Foreign Application Priority Data

Mar. 28, 2002 (DE) ......................................... 102 15 335

(51) Int. Cl.[7] ................................................ A61B 8/14
(52) U.S. Cl. ....................................... 600/443; 600/458
(58) Field of Search ................................ 600/437–472; 367/7, 11, 130, 138; 424/9.51–9.53; 128/916; 73/625–633

(56) References Cited

U.S. PATENT DOCUMENTS

| | | | |
|---|---|---|---|
| 4,509,526 A | * 4/1985 | Barnes et al. | 600/456 |
| 4,830,016 A | * 5/1989 | Tamano et al. | 600/455 |
| 5,860,931 A | 1/1999 | Chandler | |
| 5,947,904 A | 9/1999 | Hossack et al. | |
| 5,961,463 A | * 10/1999 | Rhyne et al. | 600/458 |
| 6,034,922 A | * 3/2000 | Uhlendorf et al. | 367/7 |
| 6,080,107 A | * 6/2000 | Poland | 600/458 |
| 6,234,967 B1 | * 5/2001 | Powers | 600/443 |
| 6,302,846 B1 | 10/2001 | Gardner | |
| 6,398,735 B1 | * 6/2002 | Clark | 600/458 |

* cited by examiner

*Primary Examiner*—Ali Imam
(74) *Attorney, Agent, or Firm*—Millen, White, Zelano & Branigan, P.C.

(57) ABSTRACT

In the quantification of bodies, especially bubbles, in ultrasonic diagnosis, the problem exists that the concentration of bodies, especially bubbles, is often so high that the image data that is obtained relative to the visualization becomes saturated, such that a quantification is impossible. To solve this problem, it is proposed that the bodies that are contained in the sectional layers of an object under examination first be excited by means of ultrasound to produce characteristic signals and to pick up these signals, to form data sets from the signals, to convert the data sets into an image of the body arrangement in the object under examination and to determine the number of bodies therefrom, whereby at least two ultrasonic signal sets from overlapping sectional layers in the object under examination are picked up.

21 Claims, 21 Drawing Sheets

[Key to Fig. 9:]

SAE-Schichtdicke [μm] = SAE layer thickness [μm]

[Key to Fig. 10:]

SAE-Schichtdicke [μm] = SAE layer thickness [μm]

[Key to Fig. 11:]

frame korrigiert = corrected frame

SAE-Schichtdicke [μm] = SAE layer thickness [μm]

[Key to Fig. 14:]

SAE-Schichtdicke [μm] = SAE layer thickness [μm]

[Key to Fig. 15:]

SAE-Schichtdicke [μm] = SAE layer thickness [μm]

[Key to Fig. 16:]

SAE-Schichtdicke [µm] = SAE layer thickness [µm]

[Key to Fig. 17:]

SAE-Schichtdicke [μm] = SAE layer thickness [μm]

[Key to Fig. 18:]

SAE-Schichtdicke [μm] = SAE layer thickness [μm]

[Key to Fig. 19:]

SAE-Schichtdicke [μm] = SAE layer thickness [μm]

[Key to Fig. 20:]

scan-Distanz = scanning distance

DEVICE AND PROCESS FOR QUANTIFYING BODIES BY MEANS OF ULTRASOUND

This application claims the benefit of the filing date of U.S. Provisional Application Ser. No. 60/378,358 filed May 8, 2002.

The invention relates to a device and a process for quantifying bodies that are contained in an object under examination that can be excited by diagnostic ultrasound to produce independent, characteristic signals, especially those signals that accompany the destruction of a body, preferably bubbles. The invention also relates to a use of the device for ultrasonic diagnosis and/or therapy in humans or in animals, and a use of the device and a process for in-vivo and ex-vivo mapping of physiologically upward- or downward-adjustable molecular markers in organs and tissues starting from postembryonic ontogenesis and pathologically upward- or downward-adjustable molecular markers in organs and tissues during pathogenesis and for the characterization of cell cultures by in-vitro mapping of upward- and downward-adjustable molecular markers of the cells.

Ultrasonic diagnosis has found a solid place in regular clinical practice. Details can be shown in ultrasonic images improved by injection of contrast media, since stronger ultrasonic signals can consequently be produced. As contrast media, all very small bodies (microbodies) are suitable that yield a detectable signal that can be distinguished from the tissue signal, especially very small gas-filled (micro)-bubbles. These bodies are fed to the object under examination and can be destroyed under certain conditions in the ultrasonic field, for example in the case of bubbles. In this case, these bubbles emit independent, characteristic ultrasonic signals. If the bubbles are destroyed by the ultrasonic field, the independent, characteristic signals are referred to as "stimulated acoustic emission (SAE)."

Bubbles that can emit independent, characteristic signals are described in, for example, EP 0 398 935 B1, EP 0 644 777 B1, EP 0 458 745 A1 and WO 01/68150 A1.

The principle of stimulated acoustic emission (SAE) is depicted diagrammatically in the figures below. Here, in detail:

FIG. 1: shows the principle of "stimulated acoustic emission" based on a bubble that is subjected to ultrasound, FIG. 2: shows an ultrasonic cross-sectional image from which the value of the SAE signal is evident, FIG. 3: shows a conventionally recorded ultrasonic cross-sectional image.

In FIG. 1, a first low-amplitude sound wave 1 and a second high-amplitude sound wave 2 are shown. When low-amplitude sound wave 1 is irradiated, a bubble 3 subjected thereto remains intact. In this case, a scattered signal is produced. In contrast to this, bubble 4 is destroyed when a high-amplitude sound wave is irradiated, whereby an SAE signal is produced.

SAE signals of the most varied bubbles can be detected by means of the color Doppler mode according to U.S. Pat. No. 5,425,366 A, U.S. Pat. No. 6,186,951 B1 and DE 198 13 174 A1.

Even with other ultrasonic device methods, which were originally developed primarily to visualize shift, SAE signals can be shown independently of the shift of bubbles. By way of example, the spectral Doppler method, the power Doppler method, the color Doppler method and the harmonic method ($2^{nd}$ method, sub-method, wideband method, pulse-inversion method, ultraharmonic method, color Doppler method, and harmonic-power Doppler method) can be mentioned.

The SAE signal strength is high such that individual bubbles can themselves be detected. In this case, the individual SAE signal is visualized considerably larger on the monitor (diameter about 0.5–1 mm depending on the device, transducer and settings) than that which corresponds to the actual size of the undestroyed bubble (<10 $\mu$m). In FIG. 2, the values of the SAE signals are reproduced in the cross-sectional image. In many ultrasound-diagnostic devices that are now available, the layer thickness of an individual image depending on the device setting is approximately 1 mm. This is illustrated in FIG. 3. The layer thickness of a conventional cross-sectional image can be detected there. A bubble concentration of about 2,000–3,000 bubbles/ml of tissue/blood generally results in a smooth SAE contrast in the sonographic cross-sectional image.

In the two-dimensional ultrasonic cross-sectional image, the saturation bubble concentration is determined by the layer thickness of the ultrasonic cross-sectional image (shown by way of example in FIG. 3) and the value of an SAE signal that is visualized in the ultrasonic cross-sectional image when a single bubble is destroyed (several individual bubbles are depicted in FIG. 2).

For qualitative imaging, a low saturation concentration/saturation bubble concentration may be advantageous, since in particular even at low bubble concentrations, a smooth contrast results in the cross-sectional image.

For quantifying bodies, however, a low saturation concentration/saturation bubble concentration is disadvantageous, however, since in particular even low concentrations of bodies, in particular bubbles, result in contrast saturation in the image and can no longer determine absolutely their concentrations above the saturation concentration in the image or can no longer differentiate bodies, especially bubbles.

Until bodies, especially bubbles, are dispersed only unbound in the blood, their concentration can be controlled there by the dosage in such a way that the saturation concentration/saturation bubble concentration is not achieved.

If, however, a specific or unspecific concentration of bodies, for example in cells, tissues, organs or in other accumulating structures, results, the saturation concentration/saturation bubble concentration is generally exceeded, since the accumulating tissue or the accumulating structures are so tightly packed that the bodies there accumulate at a concentration above the saturation concentration/saturation bubble concentration.

By a reduction of the dose, it was possible to go below the saturation concentration/saturation bubble concentration in the target area here under certain circumstances, but the accumulated number of bodies, especially bubbles, was at an unknown ratio to the maximum saturation. Such a measurement was therefore neither reproducible nor would it yield a value that correlates with the number of concentration factors that are present there.

A process for determination of the number of bodies (bubble number) above the saturation concentration/saturation bubble concentration is therefore desirable.

Bodies, especially bubbles, can accumulate, for example, unspecifically or specifically on or in cells, tissues, organs or other structures. This accumulation mechanism is often referred to in the literature as passive or active targeting (Lanza, G., Wickline, S.: "Targeted Ultrasonic Contrast Agents for Molecular Imaging and Therapy," Prog. Cardiovasc. Dis., 2001, 44: 13–31; Dayton, P. A., Ferrara, K. W.: "Targeted Imaging Using Ultrasound," J. Magn. Reson. Imaging, 2002, 16: 362–377).

Unspecific accumulation of bodies, especially bubbles, occurs, for example:

a) By phagocytosis of bodies/bubbles in organs of the reticuloendothelial system (RES) or in other cells that are, e.g., associated with disease, such as, e.g., in tumor-associated macrophages or macrophages in arteriosclerotic processes, or tumor cells themselves or cells that are stimulated to phagocytosis, such as, e.g., endothelial cells of the liver in certain diseases of the liver;

b) By adhesion or by slow rolling along of bodies/bubbles for example on the vascular endothelium;

c) By migration of bodies/bubbles into or through fenestrations, e.g., of the endothelium, in "vascular dead-ends" or "blind-alley" blood vessels; this can occur in the transition area to necroses, in strongly edematous or inflammatory processes, hemorrhages, hematomas or vascular bulges such as aneurysms, vessel-forming tumors such as hemangiomas or by flushing into necroses;

d) By transport of phagocytized or adherent bodies/bubbles, which are phagocytized by, e.g., monocytes or adhere to cells of the blood, such as, for example, leukocytes, by endothelial barriers, such as, e.g., the blood-brain barrier, to, for example, pathological areas.

A specific concentration of bodies, especially bubbles, can be achieved by a covalent or non-covalent bond, including an electrostatic bond, a hydrogen bridge bond or a Van der Waals bond, to physiological or pathophysiological structures. In these cases, the bodies, especially bubbles, generally carry molecules that target-specifically bind to their surface.

To measure the ultrasonic contrast, there is the possibility of digitalizing video images and of measuring the brightness (gray or color values) in image regions that can be defined over time. This type of measurement, however, does not solve the problem of contrast saturation at high concentrations of bodies/bubbles. A quantification is, if at all, possible only at very low concentrations of bodies, especially bubbles.

3D-Echotech, Halbergmoos, Germany, has also attempted to satisfy the requirement of the quantifiability of bubbles with an ultrasonic device for quantifying bubble signals in the blood. With this device, the video image of the ultrasonic device is digitalized, separated into color and gray values, and optionally evaluated according to the mean brightness value or according to the number of screen pixels within a defined measurement window (ROI). The application of this measuring system is to quantify the flooding of bubbles into blood vessels based on the brightness values within a definable ROI. This process, however, is also not suitable to quantify the bubbles above a concentration of about 3,000 particles or bubbles/ml. Even below this concentration, no reproducible measurement is possible with this device.

Kretztechnik, Zipf, Austria, offers a 3D (three-dimensional) ultrasonic process in which a 2D (two-dimensional) array (linear array, sector array, phased array, as in 2D-sonography) is automatically swiveled at a certain angle within a transducer. With this device, a quantification of bubbles can be performed in a non-reproducible manner. This applies in particular if different patients are examined and/or various examiners perform the examination.

It is not possible with any of the above-mentioned devices to quantify bodies, especially bubbles, in-vivo, ex-vivo or in-vitro, especially not in concentrations above a concentration of about 3,000 bubbles/ml of tissue or blood. Below this concentration, the spatial resolution is possible only in the millimeter range. Other measuring processes for solving this problem are not known to date.

A drawback of the known process and device therefore consists in that a visualization of small structures is not possible, since the sound lobes emitting from a transducer have minimum expansion levels that limit the resolution. For example, even the thickness of the measuring layer that is detected by the sound waves is about 1 mm in size, such that finer structures can no longer be resolved.

For the reasons above, it is not possible to use the ultrasound technology, e.g., to detect molecular markers.

Biological key technologies, such as Genomics/Bioinformatics and Proteomics, are used to identify new molecular markers (Yao, T.: "Bioinformatics for the Genomic Sciences and Towards System Biology. Japanese Activities in the Post-Genome Era." Prog. Biophys. Mol. Biol., July–August, 2002, 80 (1–2): 23–42; Wu, W.; Hu, W.; Kavanagh, J. J.: "Proteonics in Cancer Research." Int. J. Gynecol. Cancer, September–October, 2002, 12 (5): 409–423). With these technologies, the sequences, for example, of the human genes are analyzed with special bioinformatic tools to identify and to describe in detail proteins belonging to pharmacologically advantageous protein families, especially receptors and enzymes. In this in-vitro process, for example, freshly isolated (primary) cells and (immortalized) cell cultures (from diseased or healthy tissue) are used. These cell cultures are disadvantageous, however, since the expression spectrum of molecular markers can change by, for example, the isolation process. Such examined cell cultures manifest only the expression pattern of molecular markers exactly at the time at which the latter have been isolated. In addition, the cell cultures are generally immortalized cells (that can be multiplied indefinitely in vitro by special manipulation) that cannot reflect real in-vivo conditions.

Another very familiar method for identifying molecular markers is the immunohistochemical study of tissues. In this connection, especially advantageous tissues, for example from tumors, are histologically worked up after their removal and examined immunohistologically specifically for the expression of one or more molecular markers. Only after histological identification of such markers can the latter later also be manifested in vivo by using corresponding antibodies that are coupled to corresponding signal transmitters. Such imaging generally is only qualitatively possible and in most cases also only if it results in a very strong concentration of the antibody-carrying signal transmitter (Fonsatti, E.; Jekunen, A. P.; Kairemo, K. J. A. et al.: "Endoglin is a Suitable Target for Efficient Imaging of Solid Tumors: In-Vivo Evidence in a Canine Mammary Carcinoma Model," Clinical Cancer Research, Vol. 6, May 2000: 2037–2043).

At this time, many diagnostic processes for detecting molecular markers are also tested in vivo. Although the detection of known molecular markers with known diagnostic processes is possible, this process generally lacks a high spatial resolution. This is, for example, the case with PET (positron emission tomography), NIRF (near-infrared fluorescence imaging) and scintigraphy. In other cases, high concentrations of signal transmitters are required, for example with MRI (magnetic resonance imaging) and CT (computer tomography). In addition, it provides literature for use of ultrasonic contrast media in passive targeting (without antibody conjugates, e.g., without specific binding to molecular markers) and to active targeting (with antibody conjugates, e.g., with specific binding to molecular markers). None of the diagnostic processes that are described up until now, however, reach the criteria as they can be achieved with use of the device that is known from DE 102 15 335 A, namely a spatial resolution in the micrometer range and a highly sensitive quantification of signal transmitters in the target area.

The object of this invention is therefore to find a process and a device for quantifying bodies in an object under examination, with which a determination of the concentration of bodies in-vivo, ex-vivo and in-vitro above the saturation bubble concentration is possible. With the process and the device, it is to be possible to quantify element amounts in a reproducible manner and to determine their concentration. In addition, it is to be possible, relative to the independent, characteristic signals that are visualized in the video image, for example the SAE signals, to make possible a spatial resolution preferably in the histological area, also to be able to target-specifically identify, for example, molecular markers.

The object is achieved by the device for quantifying bodies that are contained in an object under examination according to claim 1, their use for ultrasonic diagnosis and/or ultrasonic therapy in humans or in animals according to claim 10, their use for in-vivo mapping and ex-vivo mapping of molecular markers in organs and tissues and in-vitro mapping of cells for the characterization of cell cultures according to claim 11 and the process for quantifying bubbles that are contained in an object under examination according to claim 12. Preferred embodiments of the invention are indicated in the subclaims.

Definitions

In this connection, reference is made in addition to the figures that are explained below. In detail:

FIG. 4: shows a color-saturated cross-sectional image

FIG. 5: shows the principle of the process according to the invention:
  a: Distance of travel: 100 $\mu$m
  b: Distance of travel: 50 $\mu$m
  c: Distance of travel: 10 $\mu$m FIG. 6: shows directions in relation to a transducer FIG. 7: shows a multielement transducer with defined, overlapping sound fields (2D-array)
  a: Image build-up with slight beam-overlap
  b: Image build-up with heavy beam-overlap FIG. 8: 3-D View of the agar phantom of Example 1 scanned with different distances of travel
  a: SAE layer thickness=10 $\mu$m to 100 $\mu$m,
    Cross-sectional image 13: distance of travel 10 $\mu$m
  b: SAE layer thickness=50 $\mu$m to 100 $\mu$m
    Cross-sectional image 14: distance of travel 50 $\mu$m
  c: SAE layer thickness=100 $\mu$m
    Cross-sectional image 15: distance of travel 100 $\mu$m FIG. 9: Dependence of MU on the SAE layer thickness
  (Agar phantom, Example 1)

FIG. 10: Dependence of the $MU_{corr.}$ on the SAE layer thickness
  (Agar phantom, Example 1)

FIG. 11: Dependence of the $SAE_{corr.}$ on the SAE layer thickness
  (Agar phantom, Example 1)

a) Bodies:
  Bodies in terms of this application are solid particles and/or bubbles with a diameter<10 $\mu$m. Solid particles contain at least one surface-active substance (e.g., surfactant), at least one carbohydrate, protein, lipid and/or natural and/or synthetic polymer.

b) Bubbles:
  Bubbles in terms of this application are gas-containing phases with a diameter<10 $\mu$m, which are either free or coated. The phases can be essentially spherical. In the case of coated bubbles, the coat can contain at least one surface-active substance (e.g., surfactant), at least one protein, lipid and/or natural and/or synthetic polymer. Bubbles according to this application can also be, for example, gas-filled microcapsules, gas-filled microparticles, gas-filled microspheres, microballoons and surfactant-stabilized microbubbles.

c) Ultrasonic Contrast Media:
  Ultrasonic contrast media are media that contain bodies, especially bubbles, for use in ultrasonic diagnosis and/or ultrasonic therapy.

d) Independent, Characteristic Signal:
  An independent, characteristic signal (CS signal, CS effect) is an echo signal of a body, especially a bubble, that is independent of a scattered signal. These also include all non-linear signals, such as, for example, $2^{nd}$ harmonic, subharmonic or ultra-harmonic, as well as especially SAE signals, as they are produced, for example, in the destruction of bubbles in the ultrasound field.

e) Stimulated Acoustic Emission (SAE)
  Bubbles that are preferred according to the invention can be destroyed under certain conditions when excited with ultrasound. In this case, an independent signal that deviates from the transmitting signal is produced that is independent of the scattering and the shift of bubbles. This independent, characteristic signal is referred to as a stimulated acoustic emission (SAE) (synonym: loss of correlation (LOC)).

f) Saturation Concentration/Saturation Bubble Concentration:
  The saturation concentration/saturation bubble concentration is the concentration of bodies/bubbles per milliliter of the object under examination, for example tissue or blood, above which it results in a superposition of the independent, characteristic signals, especially the SAE signals, within a sound field and above which a quantification of bubbles is impossible in that the number of bodies/bubbles can no longer be derived from the sum of the CS signals even using computer correction formulas.

g) CS/SAE Layer Thickness:
  For the case that the bubbles are destroyed, in this connection this is the thickness of the layer per ultrasonic cross-sectional image (sectional layer) from which the CS signals that are visualized in the cross-sectional image (in this case SAE signals) originate in a scan with parallel overlapping. For the case that the bodies/bubbles are not destroyed in the irradiation with the CS signals, this is the thickness of the layer per ultrasonic cross-sectional image, from which the CS signals that are visualized in the cross-sectional image originate in a scan with parallel overlapping of bubbles that in each case are newly added in a shift of the ultrasound field. The CS/SAE layer thickness is the same as the distance of travel per ultrasonic cross-sectional image. This layer thickness is preferably significantly less than the sectional layer. The sectional layer is produced in the object under examination by irradiation of a sound lobe (sound field). This happens in the conventional way by piezo crystal elements emitting sound pulses that are coupled by suitable media to the medium to be irradiated and are focused. By having the sound lobe that projects into the object under examination be run, for example, along the surface of the object under examination, a sectional layer from the sound lobe can be covered little by little, and the corresponding image can be generated from the acoustic signals that reach the receiver. In both above-mentioned cases, the layer thickness is defined by the feed rate between two images.

h) Region of Interest (ROI):

In this connection, this is the measurement window in the cross-sectional image.

i) Morphometric Units (MU):

Morphometric units are a measure of the surface area, corresponding to a sectional layer, expressed in the number of screen pixels, that the visualized CS signals occupy in the video image. The screen pixels are generally counted automatically by video densitometry. If the number of screen pixels of an individual CS signal is known, the body number/bubble number can be deduced from the morphometric units.

j) Corrected SAE ($SAE_{corr.}$) or Corrected MU ($MU_{corr.}$):

If the bodies/bubbles are smaller than the thickness of a layer for an ultrasonic cross-sectional image, superimposed CS signals can result in the video image. The probability of such a superposition increases with increasing concentration of bodies/bubbles and layer thickness of the ultrasonic cross-sectional image, since in this case, a larger number of bodies/bubbles is detected. Both parameters have direct influence on the percentage of color surface area of the CS signals in the video image. In the case of random dispersion of bodies/bubbles in the volume being examined, a correction of the MU when CS signals are superimposed can be carried out as follows, until complete color saturation is not present in the ROI:

$$MUcorr = \sum FP \times \left(1 + \frac{\sum FP}{\sum FP + \sum GP}\right)$$

FP: Color pixels that lie within the measurement window (ROI) in the area of the visualized CS effects, MU: $\Sigma FP$ within the measurement window (ROI), GP: Gray pixels that lie within the measurement window (ROI) but outside of the visualized CS effects.

The corrected MU ($MU_{corr.}$) in a corrected number of CS signals ($SAE_{corr.}$) can be calculated via the quotients of the sum of the color pixels and the sum of the CS signals $$\left(F_{sae} = \frac{\sum FP}{\sum sae}\right)$$

within the ROI:

$$SAEcorr = \frac{MUcorr}{Fsae}$$

The application of this correction formula requires a random dispersion of bodies/bubbles in the volume that is being examined.

k) 2D-Array:

A 2D-array consists of a one-dimensional row of piezo elements.

l) 3D-Array:

A 3D-array consists of several adjacent rows of piezo elements.

m) Transducer: (Ultrasonic Converter):

A device for sonography that contains piezo elements.

n) Directions in Relation to the Transducer:

In FIG. 6, a tranducer 23 is shown diagrammatically. The directions in relation to the transducer are defined as follows:

x=Crosswise to the transducer (reference no. 24: 2D-array)

y=Lateral (reference no. 25)

z=Axial (sound propagation direction) (reference no. 26)

o) Molecular Markers:

Intra-, inter- and/or extracellular molecular structures, for example receptors, ligands, enzymes or structural components thereof.

To be able to quantify bodies, preferably bubbles, in an object under examination, in particular those bubbles are used that can be excited to produce independent, characteristic signals and primarily bubbles that are destroyed in the irradiation.

The device according to the invention and the process according to the invention are used for quantification of bodies, preferably bubbles, that are contained in an object under examination. The device comprises at least one transducer for emitting an ultrasound field that excites the bodies, preferably bubbles, that are contained in a layer in the object under examination to emit characteristic ultrasonic signals. At least one of the transducers is also used to receive characteristic signals. Also, at least one data processing system is provided to determine the number of bodies, preferably bubbles, in the layer that consists of the characteristic signals. Also, in a way according to the invention, media are provided with which the ultrasound field can be shifted after an excitation of bodies, preferably bubbles, in a first layer in an object under examination, such that bodies/bubbles can be excited after shifting into a second layer, whereby the first layer and the second layer overlap and are shifted relative to one another in a parallel and defined manner. Ultrasonic signal data sets that consist of different sectional layers in the object under examination are thus obtained that contain information on the presence of bodies/bubbles in the individual sectional layers, especially with the spatial arrangement of the bubbles in the sectional layers. Relative to a transducer with piezo crystals that are arranged in rows, the layers are preferably displaced with respect to one another such that the piezo crystal rows overlap in the crosswise direction (x-direction).

The transducer can be designed both to emit ultrasonic signals and to receive the signals that originate from the bodies, preferably bubbles. As an alternative, the transducer can also be designed exclusively to emit ultrasonic signals. In this case, another receiver head to detect incoming ultrasonic signals from the bodies, preferably bubbles, is necessary.

To perform the process according to the invention for quantification of bodies, preferably bubbles, that are contained in the object under examination, bodies/bubbles with an ultrasound field that are contained in a layer are excited to produce characteristic ultrasonic signals. The characteristic ultrasonic signals that are sent out from the bodies/bubbles are received, and the number of bodies/bubbles is determined from the ultrasonic signals that are received, whereby in each case after bodies/bubbles are excited in a first layer in the object under examination, displacement of the ultrasound field excites bodies/bubbles in a second layer that overlaps the first layer and is displaced with respect to this layer in a parallel and defined manner.

The device according to the invention and the process according to the invention are not limited to the embodiments using imaging or the video image. The CS signals within a region of interest (ROI) can be counted already based on the receiving signals (radio frequency (RF) data), although the saturation bubble concentration when counting the CS signals on the level of the receiving signals can vary from the saturation bubble concentration when the CS signals are counted in the two-dimensional ultrasonic cross-sectional image. The device according to the invention and the counting of receiving signals can be integrated in an ultrasonic device.

In contrast to known devices and processes, it is possible with the device according to the invention and the process according to the invention also to determine concentrations of bodies, preferably bubbles, that lie above a limit that is in the range of 1000–3000 bodies (bubbles)/ml:

With known radiological and cardiological devices and processes that operate preferably in a frequency range of 2.5–12 MHz, saturation can already be observed at a concentration above approximately 1000 bodies (bubbles)/ml, such that a quantification is impossible. This depends on the spatial resolution in this case not being high enough: the spatial resolution of ultrasonic converters is namely determined by their frequency. With higher frequency, the spatial resolution increases. At the same time, however, the sonic pressure and thus the penetration depth of the ultrasonic wave in the tissue under examination are reduced. For medicinal diagnosis for which larger penetration depths are required, ultrasonic converters in the frequency range of about 2.5 MHz (tissue penetration depth of about 30 cm) to 12 MHz (tissue penetration depth of about 7 cm) are used. The spatial resolution in x-direction or x- and y-direction (in a plane perpendicular to the sound lobe) when using a single-crystal-ultrasonic converter with a round cross-section in these cases lies in the mm range. The thickness of the sound field at the most narrow point in the sound lobe that is emitted by the converter therefore also is in the mm range. For this reason, the smallest volume that can be resolved by such an ultrasonic device is about 1 mm$^3$. If a body, preferably a bubble, is destroyed in this volume by ultrasound, the exact spatial position of the corresponding CS signal cannot be determined exactly within this volume. Consequently, this signal is depicted in the image at a value that also is in the millimeter range. If at least two bodies, preferably bubbles, are found in this volume, the latter can no longer be discriminated by the ultrasonic device owing to a lack of spatial resolution. Concentrations of bodies, preferably bubbles, of more than about 1000 bodies (bubbles)/ml therefore result in saturation. This is also the reason why the above-mentioned device of 3D-Echotech is not suitable for quantifying bodies, especially bubbles, since the thickness of the sound field is in the range of about 1–2 mm. Another reason for the fact that this device is unsuitable for the quantification of bodies, especially bubbles, consists in that the transducer is guided by hand, such that some areas of the object under examination are ensonified several times or are ensonified with various degrees of overlap, while other areas are not ensonified at all. This problem is also not solved by the possibility of electromagnetic position determination of the transducer that is also developed by 3D-Echotech, since the latter is accurate only in, for example, the submillimeter range.

By this invention, a significantly higher spatial resolution than with known processes and devices is made possible for the first time. At the same time, volumes that can be calculated are taken as a baseline. As a result, a quantification of bodies, preferably bubbles, in a volume under examination is also possible for the first time if the saturation concentration/saturation bubble concentration was normally exceeded.

The Kretztechnik device is also unsuitable for quantification since the overlapping of the sound fields in axial direction (z) is not uniform. In the immediate vicinity, several adjacent sound fields almost completely overlap, while with increasing distance to the transducer, gaps develop that are then interpolated. This has the result that even the signal yield in a tissue that is examined depends on the distance to the transducer.

The above-mentioned object is achieved only by this invention.

The principle of the process according to the invention can be illustrated especially simply in the example of complete bubble destruction in each ultrasonic cross-sectional image:

With the aid of FIGS. 4, 5*b*) and *c*), the mode of operation of the invention can be shown:

a) In the first image, a contrast-saturated ultrasonic cross-sectional image is obtained (FIG. 4).

b) The bubbles are destroyed by the irradiation (FIG. 5*a*). SAE signals can then no longer be detected. Bubbles that emit independent, characteristic signals are referred to as 6; undestroyed bubbles in the non-excited sectional layer are referred to as 5.

c) Below, the sound field between two images is displaced relative to the tissue by a defined distance of travel, such that the irradiated volumes of the object under examination overlap one another, whereby the longitudinal axes of both volumes are parallel to one another. The longitudinal axis is defined as a line that runs in the direction of the sound propagation direction (direction z in FIG. 6; from the top to the bottom in FIG. 5*b*) through the middle of the sound field (in this connection, also see FIG. 7). Accordingly, in terms of this invention as a parallel shift of the two layers that overlap and from which ultrasonic cross-sectional images are obtained, it can be provided that the longitudinal axes of the two layers are parallel to one another.

d) If all bubbles were destroyed in the first image, only the new ones can be detected in the second image and all subsequent images. In a parallel shift of the sound field relative to the object under examination of, for example, 10 $\mu$m, this means that the bubbles that are newly added in the second image originate from a volume with a layer thickness of 10 $\mu$m. Since the displacement as defined above is done in a parallel manner, the entire layer thickness of the volume in which the still undestroyed bubbles are found, independently of the shape of the sound form, is extended, namely 10 $\mu$m. These still undestroyed bubbles can be quantified (FIGS. 5*b*) and *c*)). Destroyed bubbles are referred to as 7.

The principle of the process according to the invention can also be used for those bodies, preferably bubbles, that can be excited with diagnostic ultrasound to produce an independent and characteristic signal independently of a destruction. Such a signal can be, for example, a harmonic or subharmonic signal.

Here, the procedure is similar to that with an SAE signal: In the case of bubbles:

a) In the first image/a first layer, all bubbles are destroyed, b) In the subsequent images/layers, the bubbles are excited such that they give off an independent, characteristic signal, c) As long as the cumulative scanning distance is less than or equal to the layer thickness of the sound field, the newly added signals in each case are determined in each additional image/each layer, d) If the cumulative scanning distance is larger than the layer thickness of the sound field, or if a signal saturation is achieved in an image/a layer, the bubbles that are found in the sound field are destroyed.

In the case of solid particles:

a) In a first image/a first layer, no independent, characteristic signals of solid particles can be detected after excitation; this can be achieved, for example, in that the scanning is begun at a position that is free of particles or in that before the beginning of the scanning, the transducer is moved out from an area in which independent, characteristic signals of solid particles can be detected after excitation into an adjacent area in which this is not the case, b) In the following images/layers, the solid particles are excited such that they produce an independent, characteristic signal, c) As long as the cumulative scanning distance is less than or equal to the layer thickness of the sound field, the newly added signals in each case are determined in each image/each layer.

The determination of the newly added signals can, if the emitting of the signal does not accompany the complete destruction of the bodies, preferably the bubbles, be made by subtracting the respective previous value or by simple, preferably automatic counting of the signals after sending a destruction pulse.

If the independent, characteristic signals are accompanied by the destruction of the bodies, preferably the bubbles, the number of signals of the overlapping area can be determined in general as in the case of the SAE signals by simple, preferably automatic counting.

In a parallel distance of travel of 10 $\mu$m from the tissue and a layer thickness of the sound field of 1 mm, for example, the cross-sectional images (sectional layers) overlap, for example, to 99%. In the second cross-sectional image, only the newly added bodies, preferably bubbles, are detected, which are found in the 10 $\mu$m layer.

The distance of the shift between two images is at least 5 $\mu$m, preferably at least 10 $\mu$m, and especially preferably at least 20 $\mu$m. In a quite especially preferred embodiment, the distance of travel is at least 50 $\mu$m. The distance of travel is smaller than the scanning thickness (about 1–2 mm). The optimal distance of travel depends on the highest body concentration/ml, preferably bubble concentration/ml, in the scanned volume. It is advantageous to set an overlapping of volumes of between 20% and 99.99%, preferably between 40% and 99.9%, and especially preferably between 70% and 99%.

If the distance of travel is selected as too high or the ultrasonic cross-sectional images do not overlap at all (FIG. 5a), an absolute quantification is also not possible with the process according to the invention, since in the ultrasonic cross-sectional image, a superposition of the C S signals that cannot be corrected occurs.

The distance of travel can be selected, for example, as too high, or the ultrasonic cross-sectional images optionally cannot overlap at all if the degree of concentration of the bodies, preferably bubbles, is underrated. In these cases, the distance of travel per ultrasonic cross-sectional image must be reduced to ensure the absolute quantifiability. FIGS. 9 to 11 show the connection between the distance of travel and the morphometric units (MU) or the number of independent, characteristic signals in the cross-sectional image.

The concentration of bodies, preferably bubbles, is preferably determined in those CS/SAE layer thicknesses whose cross-sectional images in each case have 20 to 80%, preferably 30 to 70% color saturation. In favor of a reduced examination time, the distance of travel can be increased, however, until the saturation bubble concentration is not reached in any cross-sectional image. A defined program that varies the CS/SAE layer thickness can provide for an optimal compromise between examination time and exactness of the measurement. The optimal distance of travel that is controlled by the program can be determined, for example, based on an adequately large population of patients (objects under examination).

If individual contrast-saturated cross-sectional images accidentally result, however, the absolute quantifiability is no longer provided. A quantifiability on the non-contrast-saturated cross-sectional images remains possible, however.

Even if a color saturation is present in certain areas of the examination area, a reproduced measurement is possible by the standardized scanning process with defined parallel shift of the sound fields and the higher spatial resolution of the process according to the invention. Such a measurement can be sufficient, e.g., for a comparison between different patients or for a monitoring of the course of therapy in the same patients.

If not all bubbles are destroyed in a cross-sectional image, one or more additional destruction pulses can also be transmitted before approaching the next position.

The overlapping and displacement of the volumes of the sectional layers can be achieved in that the transducer and the object under examination are shifted against one another (relative to one another).

The defined parallel displacement can be achieved, in which

I. The tissue or the object under examination, for example a patient, is shifted relative to the fixed transducer, or II. The transducer is shifted relative to the fixed object under examination, for example a tissue, that is to be examined, or III. A transducer is used that is able to produce cross-sectional images that successively overlap and are offset in time, i.e., the volumes are shifted with a transducer and caused to overlap, whereby the transducer itself receives overlapping and parallel-shifted ultrasonic images; in this connection, the transducer can be controlled such that the overlapping and in particular crosswise-shifted ultrasonic cross-sectional images or sound lobes of a sectional layer are picked up.

The various shift possibilities can also be combined.

By way of example, the following variants of a parallel shift can be described:

I. The object under examination (patient, animal, an eviscerated or isolated organ or a cell culture dish) is automatically moved past the fixed transducer (e.g., by servomotor or DC motor).

II. The transducer is automatically shifted with the aid of a special device over the, or relative to, the object under examination (patient, animal, an eviscerated or isolated organ or a cell culture dish). The device can be a frame within which the transducer is fixed in a holding device and is moved along a parallel guide by a motor.

In the simplest case, an individual crystal can be shifted in x- and y-direction with defined overlapping areas. This variant is presented for, e.g., culture dishes of cells on whose surface bodies, especially bubbles, have specifically accumulated or in whose interior bodies have unspecifically accumulated, for example by phagocytosis. Here, the statement on how many bodies, especially bubbles, per surface area or volume have accumulated is sufficient. The data must not be converted into images.

In addition, with a transducer that contains a 2D-array, adjacent sound lobes within a line can be caused to overlap in the crosswise direction in a defined manner by directing the scan accordingly.

III. With a transducer that contains a 3D-array, adjacent sound lobes within a line or sound lobes of adjacent lines can be caused to overlap in the crosswise direction in a defined manner by directing the scan accordingly. In this variant, another movement of the transducer or object under examination is no longer necessary.

The transducer can also contain a 2D-array that is moved in parallel in the crosswise direction (x-direction) within the transducer with defined overlap. The lateral resolution can be increased within a 2D-cross-sectional image, if the individual scan lines, from which the cross-sectional image is built up, also overlap in a defined manner. The individual sound fields, which are produced in each case from a group of adjacent piezo elements, in this case are stronger in contrast to the conventional control and are primarily caused to overlap in a defined manner by small step widths (down to a piezo element) being selected.

This is shown, for example, in FIG. 7: From an array of individual piezo elements 11, a smaller area 12 of piezo elements, comprising fewer array elements, is excited to produce oscillations (FIG. 7a). As a result, a sound wave in the form of a sound lobe 9 is emitted in the object under examination.

Undestroyed bubbles 8 that are found within the sound lobe are destroyed and thus emit independent, characteristic signals 9. The destroyed bubbles are referred to with reference no. 10. Then, a newly formed group of piezo elements of the array is excited to produce oscillations that are distinguished from the group that is used in the first excitation only by one piezo element, by which the group is now offset (FIG. 7b). By the overlapping of the thus produced sound lobe with the previously emitted sound lobes, the newly detected bubbles are only excited to produce independent, characteristic signals.

As in the defined overlapping scan in the crosswise direction to the transducer, the resolution is increased by the factor in which the displacement is in the width of the piezo-element group.

To shift the transducer and/or the object under examination, at least one motor drive is therefore provided to shift the object under examination or at least one transducer relative to one another.

If the transducer is to be shifted relative to the object under examination, the latter must be moved in a defined way. In this connection, a movable holding device for the transducer is provided. The object under examination is set in a holding device. It is, of course, not absolutely necessary to secure the object under examination by gripping, clamping or another similar attachment with the holding device. It is also sufficient that the object is held virtually immobile by the holding device. For example, a patient can be placed on a couch on which the latter rests during the examination. Such holding devices can then be used for holding the object under examination both if the latter is not moved during the examination, but rather only the transducer, and if the object under examination is moved and the transducer is not. Also, for the case that both the transducer and the object under examination are moved simultaneously relative to one another, the above-mentioned holding devices can be used for the object under examination.

To quantify the bodies, preferably bubbles, an image evaluation system for data processing and image display is provided in a preferred embodiment with which the quantification can be implemented by video densitometry. In this connection, the data sets that are formed from the ultrasonic signal sets are converted in a known way such that a video image of the individual sectional layers is produced, whereby each sectional layer contains the information from the areas that does not overlap a preceding excited sectional layer (by displacement of a new sectional layer area reached (CS/SAE layer)). The bodies, especially bubbles, that are visualized in the individual video images can then be counted manually or can be obtained by videodensitometric determination of the color pixels and division of the value obtained therefrom by the mean number of the color pixels per bubble visualization.

Since the number of bodies, preferably bubbles, had been determined according to above-described methods, it may be necessary, for a corrected determination of the number, to make a correction according to the following formula:

$$MUcorr = \sum FP \times \left(1 + \frac{\sum FP}{\sum FP + \sum GP}\right)$$

whereby

FP are the color pixels that visualize the body signals, especially bubble signals, in a screen visualisation with local resolution within the overlapping layers, and GP are the gray pixels in a screen display with local resolution that are not the pixels that visualized the bodies, especially bubbles.

The device according to the invention is suitable in particular for ultrasonic diagnosis and/or ultrasonic therapy in humans or in animals.

New possible avenues of research are opening up not only in the areas of clinical diagnosis, but also in basic medical and biological research and preclinical research and development.

The bodies, preferably bubbles, can be quantified in vivo in the animal test, ex vivo in the organs or tissues that are removed, as well as in vitro, e.g., in cell cultures to clarify pathological or physiological processes on the molecular level.

In finding active ingredients and development of specific binding systems, an examination can be made with the process according to the invention as to which binding systems function at all, which binding molecules are present under which conditions at which points in which amounts, which influencing variables determine the binding ability and concentration, which kinetics the bodies, preferably bubbles, have or, in the case of ultrasound-induced active ingredient release, how much of an encapsulated active ingredient is released.

The device according to the invention and the process according to the invention can be used for, for example, the in-vivo mapping of physiologically upward- or downward-adjustable molecular markers in organs and tissues starting from postembryonic ontogenesis (ontogenesis: totality of the development of an independent chemical compound from the unfertilized/fertilized ovocytes until natural death: the latter comprises four phases: 1. embryonic development, 2. postembryonic development, 3. time of sexual maturity and reproduction and 4. time of aging).

In this connection, both passively and actively accumulating bodies, preferably bubbles, can be used: for this purpose, the bodies can be provided with specific binding molecules for the markers that are found on the surface (bodies/bubbles that can accumulate actively). In an alternative embodiment of the invention, bodies that accumulate passively can also be used, i.e., bodies/bubbles without such specific binding molecules.

With this process, molecular markers can be located in vivo on different cells in humans and in animals, and their influence on ontogenesis can be determined.

A time-controlled mapping of known and newly identified molecular markers in the total organism in vivo can also be performed. As a result, a still not yet known function of the molecular markers in ontogenesis in vivo can be determined For gerontology, an identification of molecular markers in the $4^{th}$ phase of the ontogenesis (time of aging) and its influence on the aging process is especially advantageous. In this connection, by means of high-spatial-resolution sonography according to the invention, it can be examined from which age manifestations these molecular markers originate and in which the latter can result, also which basis these receptors show for age-induced changes or diseases of the overall organism and whether findings for the development of medicines can be derived therefrom, alleviate or even help to avoid the age-induced symptoms.

In another advantageous use of the device according to the invention and the process according to the invention, an in-vivo mapping of pathologically upward- or downward-adjustable molecular markers in organs and tissues can be implemented during pathogenesis, also with use of bodies, especially bubbles, that can be accumulated passively and actively.

With this process, disease-associated molecular markers can be located in vivo on different cells in humans and in animals, and therefore their influence on pathogenesis of diseases can also be determined in vivo.

In addition, a time-controlled mapping of known and newly-identified disease-associated molecular markers can be implemented in the total organism during pathogenesis in vivo. As a result, a still not yet known function of the molecular markers in pathogenesis can be determined in vivo.

Also, new therapeutic medications and/or treatment strategies can be derived from these findings, such that at certain times, the determined surface states of cells (status of cells relative to the activation/the at-rest position) are regulated, and these conditions are tracked with the process according to the invention.

Finally, a highly sensitive monitoring of the course of therapy in vivo is also possible such that the surface states of the cells are tracked.

The processes above can also be performed ex vivo on organs and tissues that have been removed.

The in-vivo mapping of molecular markers in the organs and tissues starting from postembryonic ontogenesis and during the pathogenesis can be used, of course, on different animal types and/or animal models, in particular in gerontology or for a disease model. The mapping can generally also be used for all animal types, for example, farm animals, domestic animals and pets, as well as wild animals, and for humans. Since the mapping can be used in vivo, it is unnecessary in many cases to use time-intensive and costly conventional in-vitro processes, for example immunohistochemistry, which are often associated in addition with the drawback that it is necessary to identify and characterize molecular markers at exactly one point in time.

In addition, the device according to the invention and the process according to the invention also can be used to characterize cell cultures by in-vitro mapping of upward- and downward-adjustable molecular markers of cells of different origins, for example under various cultivation conditions or for characterization of new cell lines or for new characterization of existing cell lines after various passages or directly before use thereof, especially in the implantation of tumor cells in mice, rats and other animal models. In this case, in addition to animal and human cells, plant cells can also be characterized.

Also in this case, the bodies, preferably bubbles, are provided with binding molecules that are specific for markers.

To identify molecular markers in the respective areas of use, reference is made expressly to the following publications by way of example, which are included herewith as a reference in the disclosure content of this application, whereby the question-statements described therein can be examined with the device and with the process according to this invention:

1. Phelps, M.: "Positron Emission Tomography Provides Molecular Imaging of Biological Processes." Proc. Natl. Acad. Soc., USA 2000, 97:9226–9233.
2. Weissleder, R., "Molecular Imaging: Exploring the Next Frontier." Radiology, 1999, 212:609–614.
3. Bremer, C., Tung, C. H., Weissleder, R., "In Vivo Molecular Target Assessment of Matrix Metalloproteinase Inhibition." Nat. Med., 2001, 7:743–748.
4. Anderson, S. A., Rader, R. K., Westlin, W. F., et al., "Magnetic Resonance Contrast Enhancement of Neovasculature with $Alpha_v\beta_3$-Targeted Nanoparticles." Magn. Reson. Med., 2000, 44:433–439.
5. Sipkins, D. A., Cheresh, D. A., Kazemi, M. R., Nevin, L. M., Bednarski, M. D., Li, K. C., "Detection of Tumor Angiogenesis In Vivo by alphaVbeta3-Targeted Magnetic Resonance Imaging." Nat. Med., 1998, 4:623–626.
6. Bredow, S., Lewin, M., Hofmann, B., Marecos, E., Weissleder, R., "Imaging of Tumour Neovasculature by Targeting the TGF-[beta] Binding Receptor Endoglin." Eur. J. Cancer, 2000, 36:675–681.
7. Sipkins, D. A., Gijbels, K., Tropper, F. D., Bednarski, M., Li, K. C. P., Steinman, L., "ICAM-1 Expression in Autoimmune Encephalitis Visualized Using Magnetic Resonance Imaging." J. Neuroimmunol., 2000, 104:1–9.
8. Lindner, J. R., Song, J., Christiansen, J., Klibanov, A. L., Xu, F., Ley, K., "Ultrasound Assessment of Inflammation and Renal Tissue Injury with Microbubbles Targeted to P-Selectin." Circulation, 2001, 104:2107–2112.
10. Klibanov, A. L., Hughes, M. S., Marsh, J. N., et al., "Targeting of Ultrasound Contrast Material: An In-Vitro Feasibility Study." Acta Radiol. Suppl., 1997, 38:113–120.
11. Demos, S. M., Dagar, S., Klegerman, M., Nagaraj, A., Mcpherson, D. D., Onyuksel, H., "In Vitro Targeting of Acoustically Reflective Immunoliposomes to Fibrin under Various Flow Conditions." J. Drug Target., 1998, 5:507–518.
12. Villanueva, F. S., Jankowski, R. J., Klibanov, S., et al., "Microbubbles Targeted to Intercellular Adhesion Molecule-1 Bind to Activated Coronary Artery Endothelial Cells." Circulation, 1998, 98:1–5.

The device and the process allow or support the quantifiability of bodies, preferably bubbles and thus also, for example:

A determination of tumor dignity,

A staging of tumors,

A monitoring of the course of therapy, e.g., in the case of chemotherapy,

An increase in reproducibility and thus the ability to compare findings of different examiners, An avoidance of biopsies, which are a burden on the patients, A reduction of layer thickness, from which the CS signals that are visualized in the ultrasonic image originate, by which bubble concentration fields in the millimeter range with high spatial resolution in the micrometer range are imaged and can be quantified relative to the bubble concentration.

The bodies, especially bubbles, are generally contained in ultrasonic contrast media and are administered preferably in the form of suspensions.

In principle, all bodies, especially (micro)bubbles, that are suitable for use as ultrasonic contrast media, can be excited with diagnostic ultrasound to produce CS effects. For the commercially available ultrasonic contrast medium Levovist® (Schering AG, Berlin), which contains microparticles from galactose and palmitic acid and produces a suspension of stabilized gas bubbles after water is added, CS effects were also observed after unspecific concentration in the liver (Blomley, M. J. et al.: "Stimulated Acoustic Emission to Image a Late Liver and Spleen-Specific Phase of Levovist in Normal Volunteers and Patients with and without Liver Disease." Ultrasound Med Biol., 1999 November: 25(9): 1341-.

Particulate ultrasonic contrast media that contain bubbles in the form of gas-filled microcapsules or gas-filled microparticles, whose shell consists of polyalkylcyanoacrylates, especially polybutylcyanoacrylate, are preferred according to the invention. The latter are described in EP 0 644 777 B1, especially in the examples: Then, cyanoacrylic acid alkyl ester, for example cyanoacrylic acid butyl ester, is dispersed in acidic aqueous solution, which in addition contains a surfactant. The microparticles that are produced can be obtained by centrifuging. Especially preferred are bubbles with functionalized polyalkylcyanoacrylates, which are produced according to the process described in WO 01/68150 A1. Therefore, the process that is described there is expressly incorporated into the disclosure contents of this application. For the production of the bubbles that are preferred according to the invention, the polymers that are described in WO 01/68150 A1 are used. These starting substances for the production of bubbles are therefore also recorded expressly in the disclosure contents of this application.

The process according to the invention can also be used for ultrasonic contrast media that contain various types of bodies, preferably types of bubbles.

The bodies can vary in at least one of the following features:

Type of solid material,
Size,
Binding molecules on their surfaces,
Excitability by various pulse forms,
Destructibility by sound,
Type of characteristic signal,
Type of gas in the body/bubble,
Type of shell of a body/bubble, e.g., material thickness, elasticity.

For example, such bubble mixtures or distribution patterns thereof in the object under examination can be quantified with the process according to the invention also with higher spatial resolution, a) By various pulse forms being transmitted in a position behind one another and/or various characteristic signals being received; in this case, this results not only in a complete destruction of the bubbles, but a destruction pulse can be transmitted before moving on to the next position, or b) By the field that is to be examined being scanned several times with correspondingly defined shifting, whereby each scan is performed with another pulse form that is necessary to the respective type of bubble.

Both various pulse forms and various sound field shifts can be combined with one another, until the resulting overlapping of the sound fields is defined and is carried out in a calculable manner in reference to their spatial expansion and until the bubbles that are used can be detected based on characteristic signals.

If the bubbles are distinguished simultaneously in the binding molecule on the surface and in their destructibility by sound, to determine the in-vivo, ex-vivo and in-vitro dispersion of the binding sites in the examination region, the procedure can be as follows:

a) Two different types of bubbles are injected:
   i. Bubble type A, which can be destroyed with low sonic pressure and with a binding molecule Anti-X for in-vivo binding site X on the surface, and
   ii. Bubble type B, which can be destroyed with high sonic pressure and with a binding molecule Anti-Y for in-vivo binding site Y on the surface, b) Approach to the calculated position, c) Recording of one or more images with low sonic pressure, and data storage, d) Recording of one or more images with high sonic pressure, and data storage, e) Defined shift of the sound field, f) Repetition of steps c)–e) until the end of the scan, g) Evaluation of the data for binding molecules X and Y, their indicators on the monitor and storage.

In all of the above-mentioned variants, the saturation bubble concentration is increased by the factor in which the distance covered between two images or sound lobes in each case relates to the layer thickness of the entire sound field. In the case of a 10 $\mu$m shift and a 1 mm layer thickness, the saturation bubble concentration is increased by a factor of 100. At the same time, the layer thickness of the tissue from which the newly added bubbles originate is reduced by the same factor.

A histological resolution can thus be achieved. Since this principle can also be applied in vivo, it is also possible to speak of an "in-vivo sono-histology" or, in the case of a specific bubble accumulation, a sonographic "in-vivo immuno-histology" relative to the visualized signals.

The measured MU can also be evaluated for a diagnosis, for example, as follows:

A. Comparison of the measured MU at a CS/SAE layer thickness and a dose that are kept constant for intraindividual monitoring of the course of a therapy.

B. 1) First, determination of the dependence of the measured MU on the CS/SAE layer thickness and/or dose in a special measurement window (liver, tumor surface area, vascular endothelium, etc.) based on as large a population as possible. The population can consist of individuals that are not distinguished with respect to the dispersion and the degree of concentration of the bubbles in the measurement window, i.e., that is homogeneous or else that is grouped in this connection. These dependencies generally must be determined at various ultrasonic device settings (transducer, detection mode, etc.).

2) Determination of linear correlation functions in the range of 20 to 80%, preferably in the range of 30 to 70% color saturation.
3) Optionally, integration of the linear correlation functions in an evaluation software of the ultrasonic device.
4) Counting of the CS signals in the corresponding measurement window of an object under examination, for example a patient.
5) Based on the linear correlation functions: determination of the absolute number of bubbles or the bubble concentration in a special measurement window of the patient, if color saturation is in the range of the linear correlation function.

C. 1) First, determination of the dependence of the absolute counted CS signals from the CS/SAE layer thickness and/or dose in a special measurement window (liver, tumor surface area, vascular endothelium, etc.) based on as large a population as possible. The population can consist of individuals that are not distinguished with respect to the dispersion and the degree of concentration of the bubbles in the measurement window, i.e., that is homogeneous or else that is grouped in this connection. These dependencies generally must be determined at various ultrasonic device settings (transducer, detection mode, etc.).
2) Implementation of curve fit, determination of the correlation functions described by the respective curve.
3) Optionally integration of the correlation functions in an evaluation software of the ultrasonic device.
4) Counting of the CS signals in the corresponding measurement window of a patient.
5) Based on the correlation functions: determination of the absolute number of bubbles or the bubble concentration in a special measurement window of the patient.

The invention is to be confirmed with the following examples without the scope of protection of the invention thus being limited. To this end, reference is also made to the figures below by way of explanation. In particular:

FIG. 12 shows bubble accumulation in the liver, rat 1 (Example 2): $1*10^8$ bubbles/ml; ex-vivo measurement, 30 minutes p.i.
a: SAE layer thickness=about 1 mm
b: SAE layer thickness=20 μm FIG. 13 shows bubble accumulation in the liver, rat 2 (Example 2): $1*10^7$ bubbles/ml; ex-vivo measurement, 30 minutes p.i.
a: SAE layer thickness=about 1 mm
b: SAE layer thickness=20 μm FIG. 14 shows dependence of MU on the SAE layer thickness
Rat 1 (Example 2): $1*10^8$ bubbles/ml; ex-vivo measurement, 30 minutes.

Figure 20:
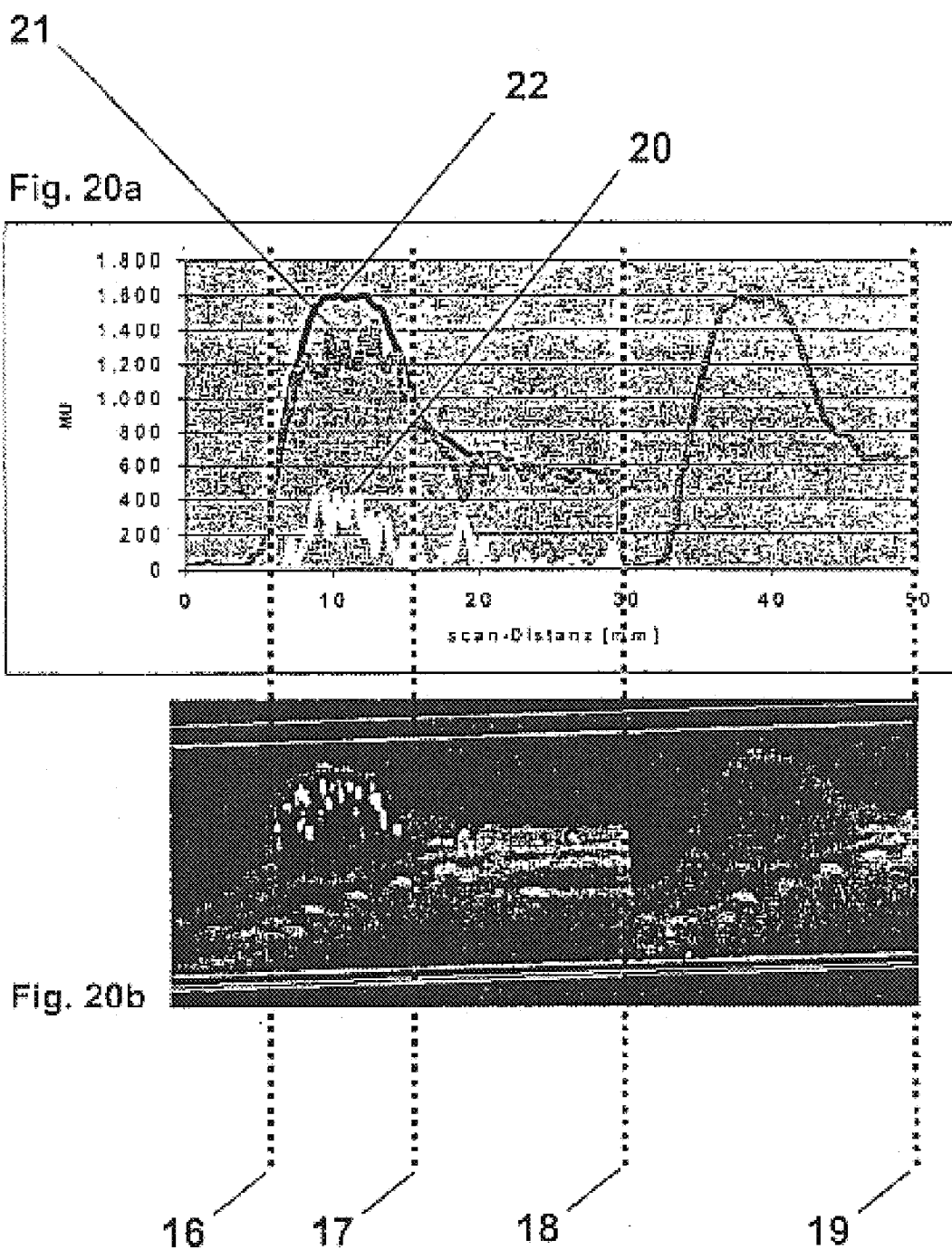

FIG. 20 shows accumulation of specific bubbles to whose surface anti-CD-105 antibodies are coupled in the F9-ter atom of a mouse (Example 3)
a: Graphic visualization
b: Sonagraphic longitudinal section of the tumor in scanning direction
Area between lines 16 and 17: tumor during the first scan
Area between lines 18 and 19: tumor during the second scan FIG. 21: Color signals of the specific bubbles that are accumulated in the tumor (four mice, Example 3), in comparison to the isotype control (four mice, Example 3).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius, and all parts and percentages are by weight, unless otherwise indicated.

EXAMPLE 1

Agar Phantom that Contains 30,000 Bubbles/ml
(a) Production of Bubbles:
The bubbles are produced according to Example 4(a).
(b) Production of the Agar Phantom that Contains 30,000 Bubbles/ml:

665 ml of water (Ampuwa®, Fresenius) was boiled in a boiler (Braun, Type 3 217 WK 210) and moved into a 1000 ml beaker. 1.7 g of benzoic acid (Merck) was added for preserving, and 10 g of agar (Merck) was added while being stirred. The agar solution was briefly boiled again in a microwave (Bosch HMT 702 C, 800 W) and then cooled to 40° C.

Before the bubbles were added to the agar solution, the bubble concentration was adjusted with 0.02% (m/m) Triton X 100 solution to $6*10^8$ bubbles/ml. 33 μl ($2*10^7$ bubbles) therefrom was carefully stirred into the agar solution without introducing air bubbles. The agar solution was then poured into a glass dish (14 cm*19 cm*4 cm), in which the latter solidified as a gel (agar phantom).

(c) Experimental Set-Up and Implementation:
An approximately 4 cm strip of the agar phantom was put into a plastic basin that was filled with water. A transducer (L 10-5, ATL UM9, color Doppler mode, MI: 1.1, persistence: 0, priority: maximum, size of the color box: maximum, penetration depth: 3 cm, focus: 2 cm) was fastened vertically with a support stand via the phantom in such a way that it was immersed in the water.

The basin, together with the phantom, was
1. shifted by hand in the crosswise direction under the transducer at a speed of about 2 cm/s, which corresponded to a distance of travel of about 1 mm/frame, or
2. was set on a servomotor (Limes 150, OWIS GmbH, Motor controller DC 500) and automatically moved past at different speeds under the fixed transducer. The speeds were selected in this case such that by taking into consideration the given image rate of the ultrasonic device of 5.8 images/second and continuous motion of the agar phantom, the following distances of travel per image resulted: 10, 20, 30, 40, 50, 60, 70, 80, 90, 100 μm/frame. The speeds that were necessary for this purpose (μm/s) were calculated as follows:

Speed [μm/s]=distance of travel/image [μm/frame]×image rate of the ultrasonic device [frame/s]

(d) Quantification of the SAE Signals:

The video images that were produced were evaluated as follows by video densitometry with QuantiCon© (Echotech 3D Imaging Systems GmbH):

During the scan, the video images were digitalized at a sample rate that corresponds to the image rate that is provided by the ultrasonic device (here, 5.8 images/second) (QuantiCon). To this end, a trigger-delay of 172 ms (1000 ms/5.8) was input into QuantiCon in advance.

Figure 1:
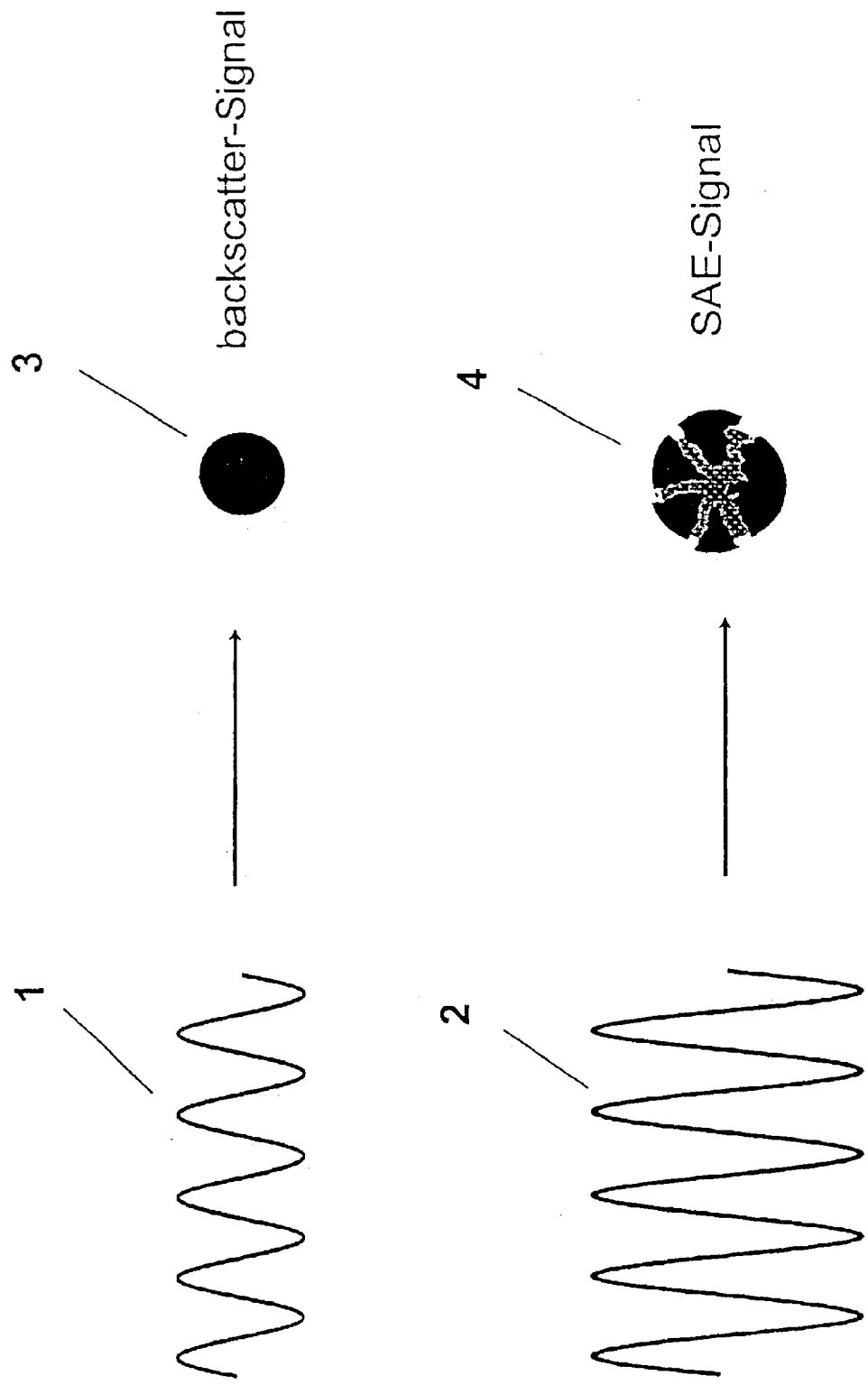
Figure 2:
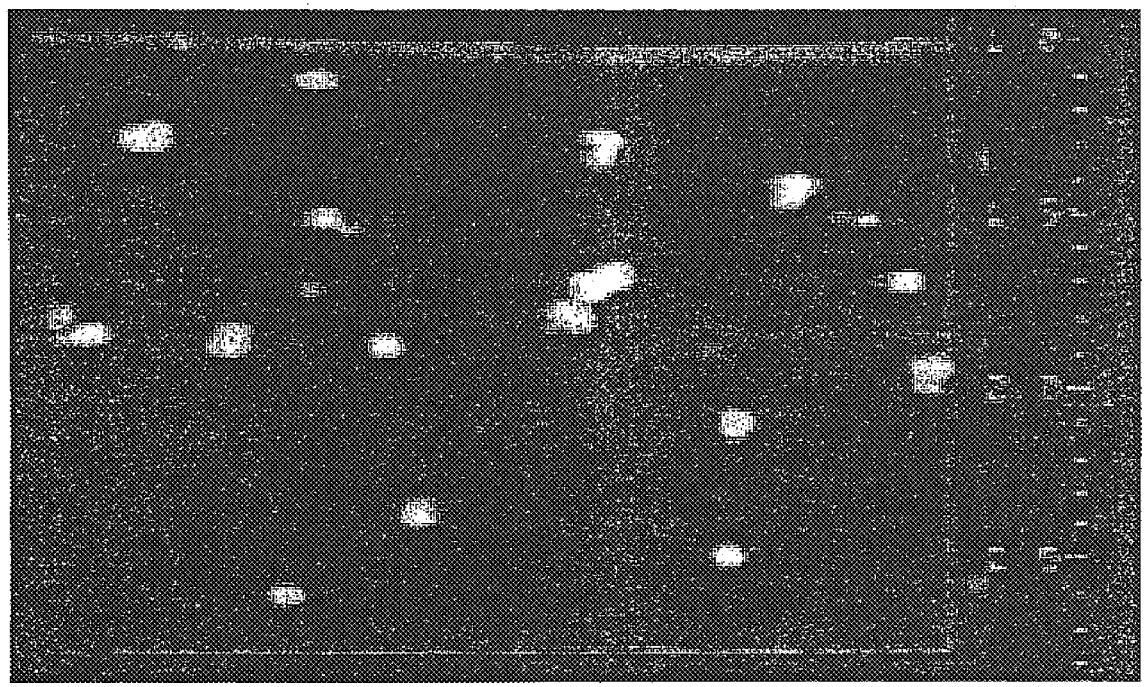
Figure 3:
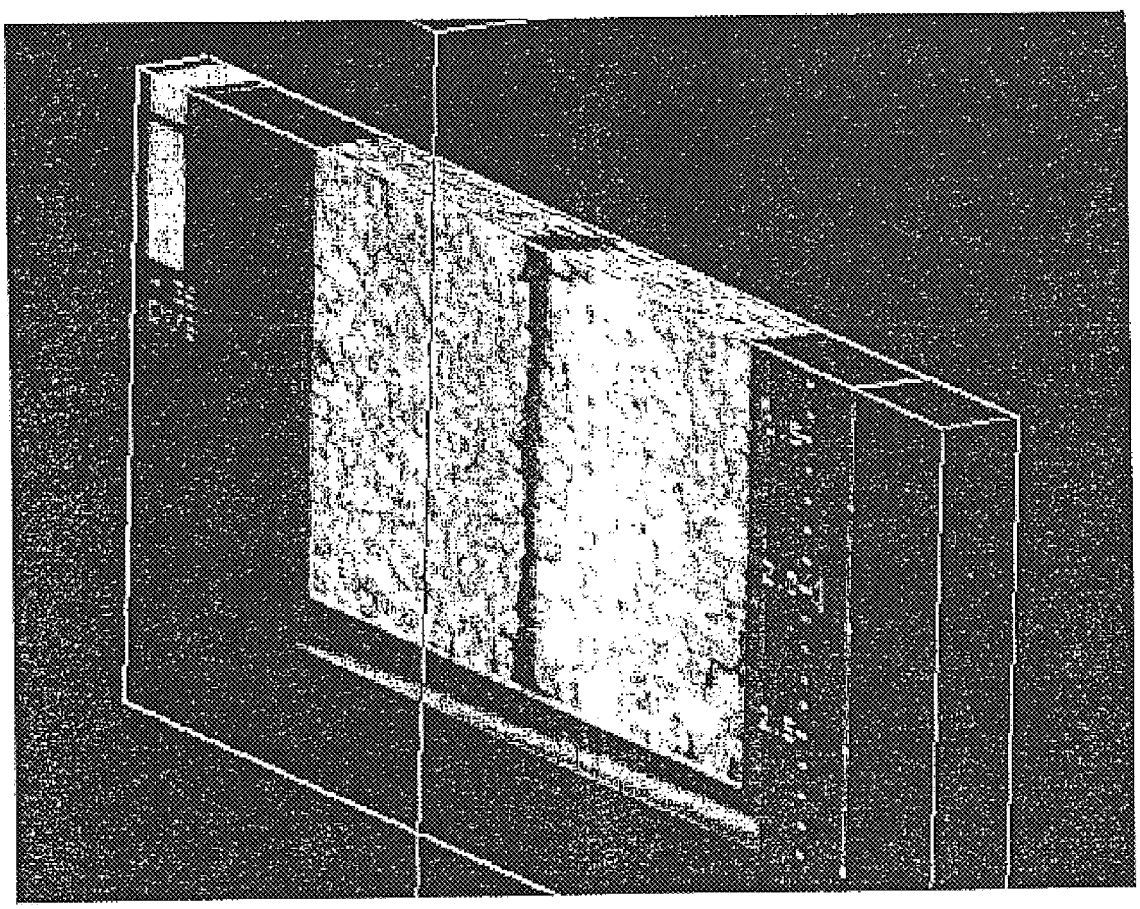
Figure 4:
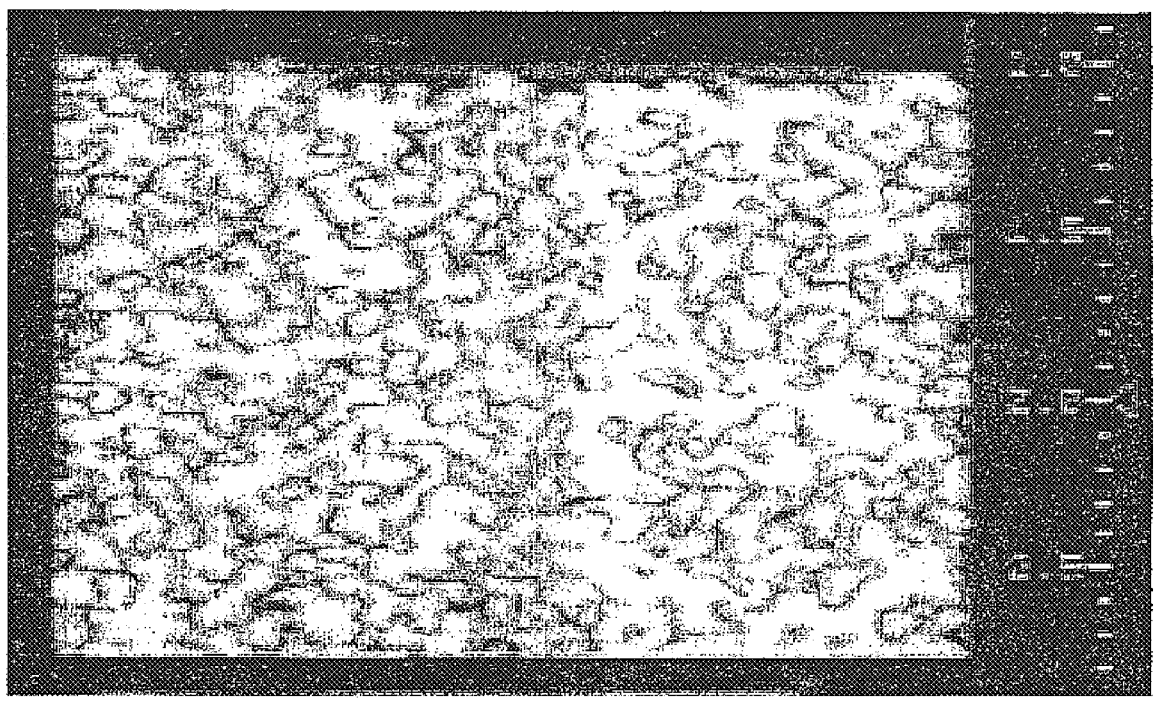
Figures 5A, 5B, 5C:
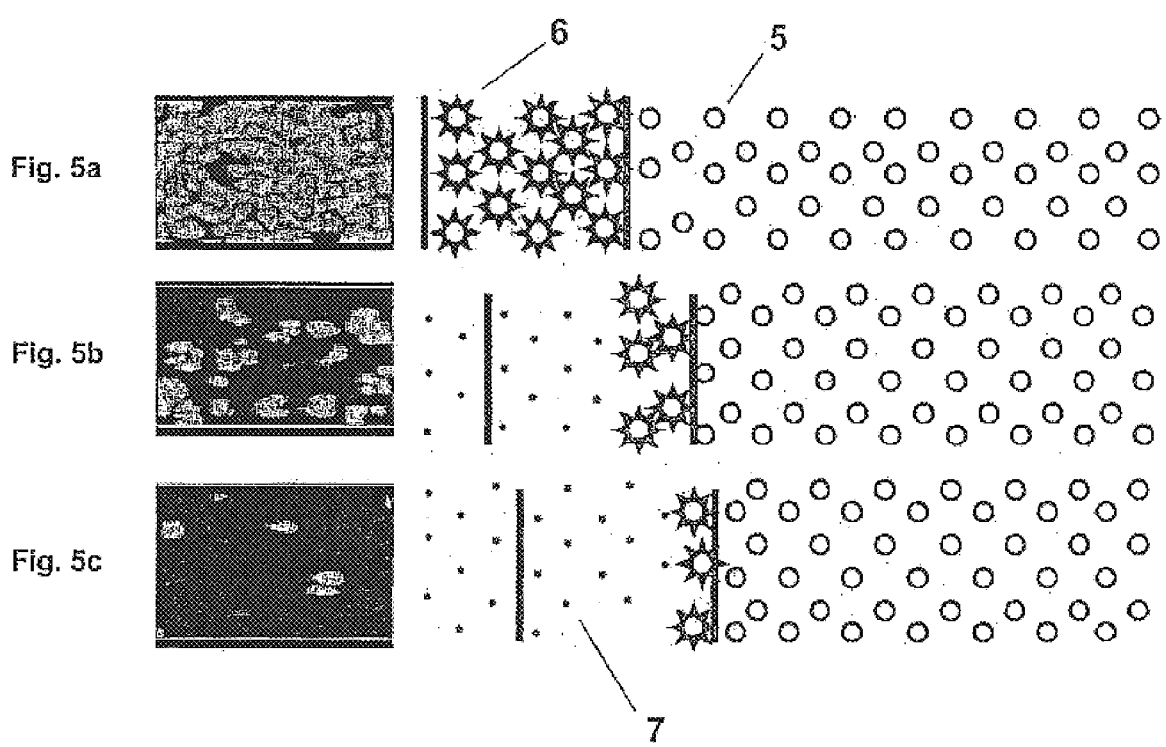
Figure 6:
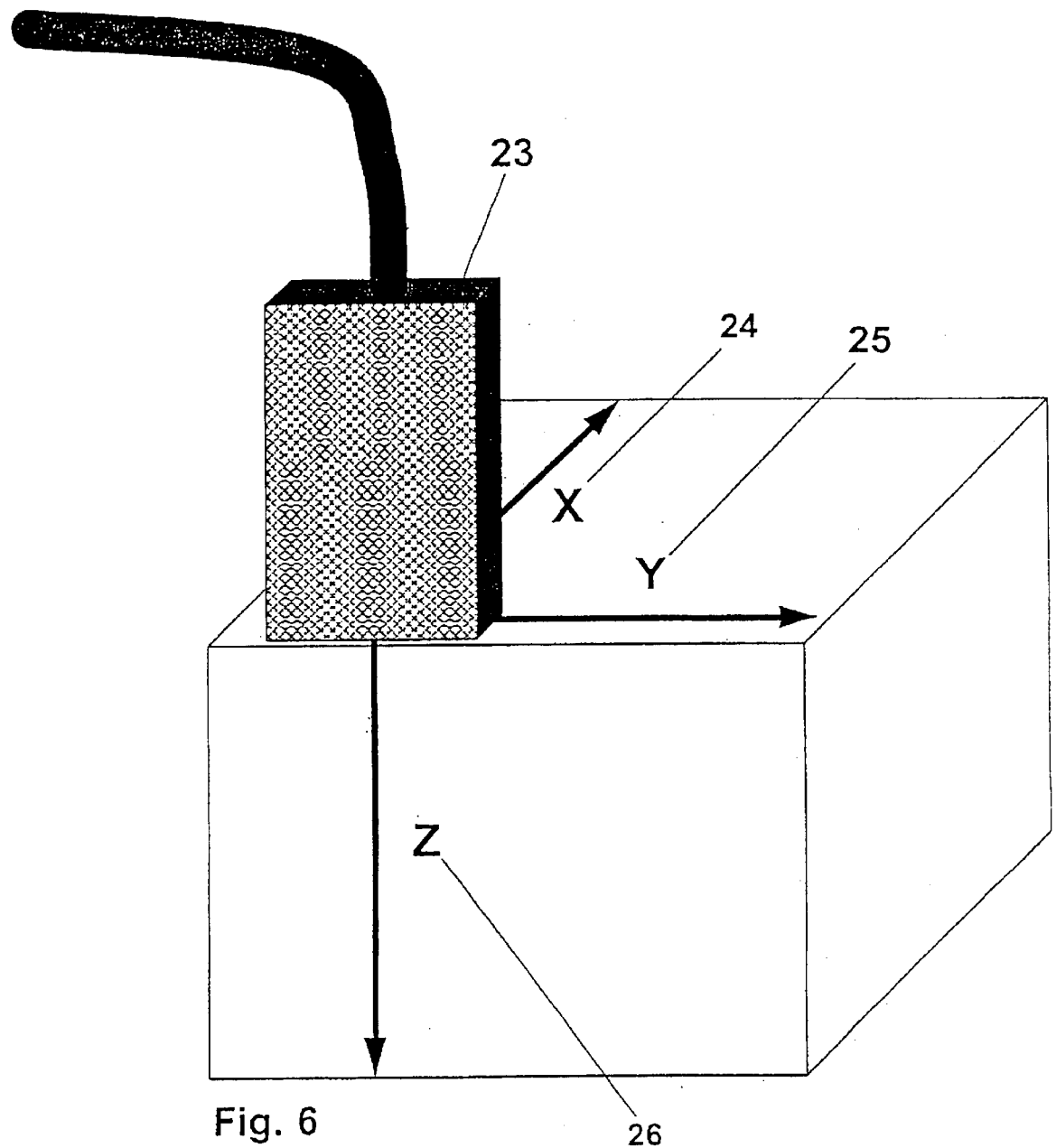
Figure 7A:
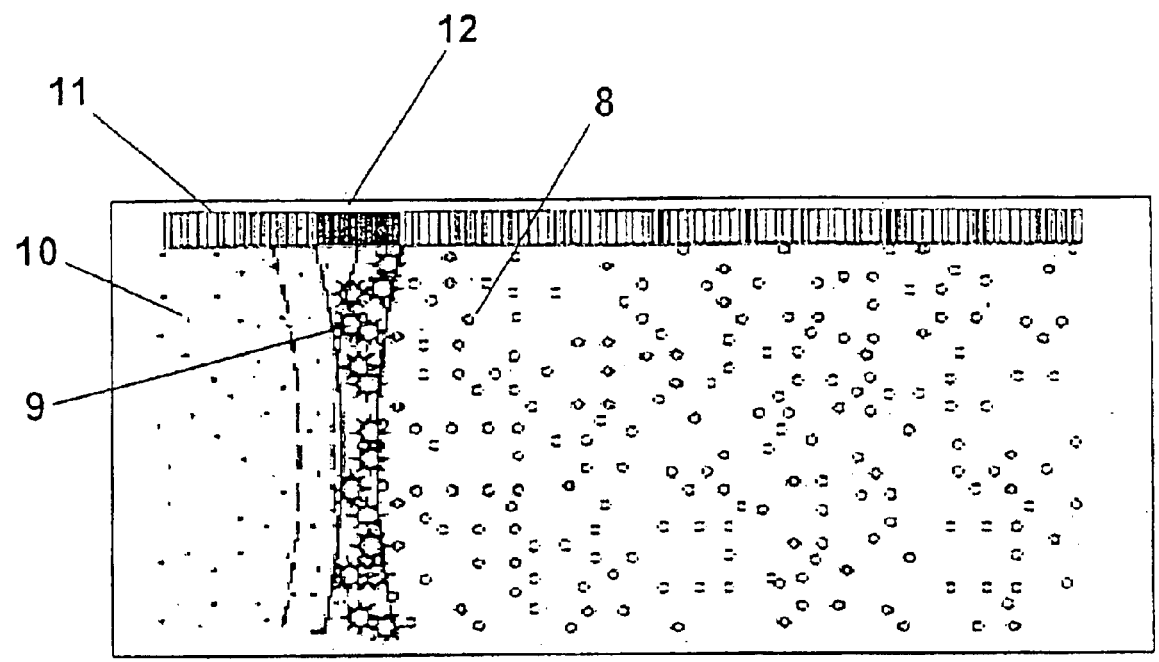
Figure 7B:
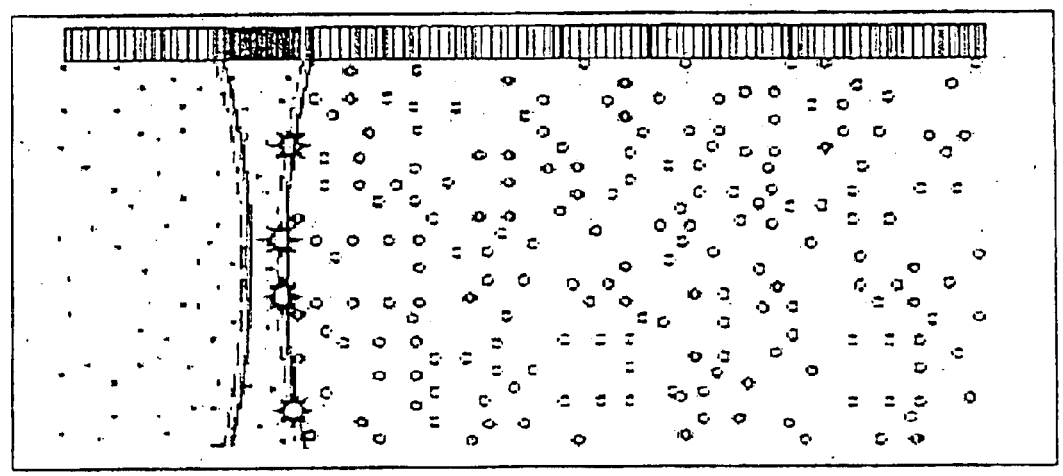
Figure 8A:
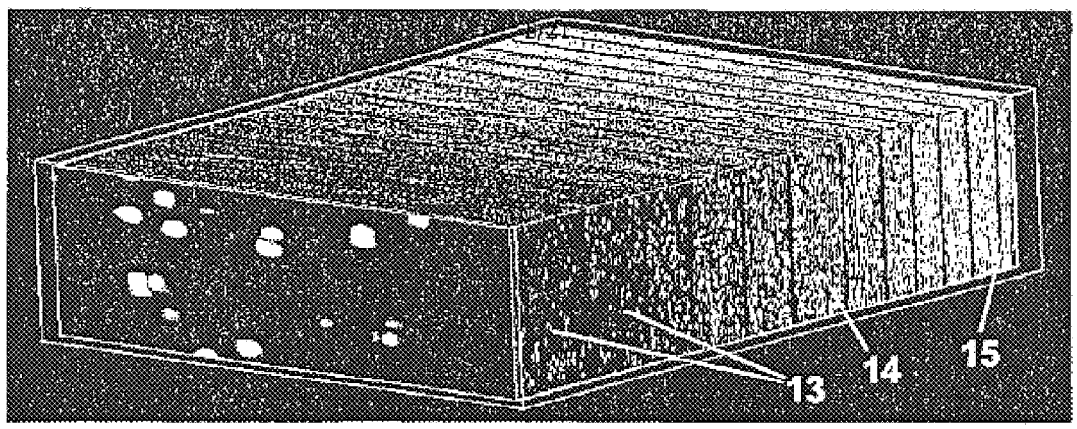
Figure 8B:
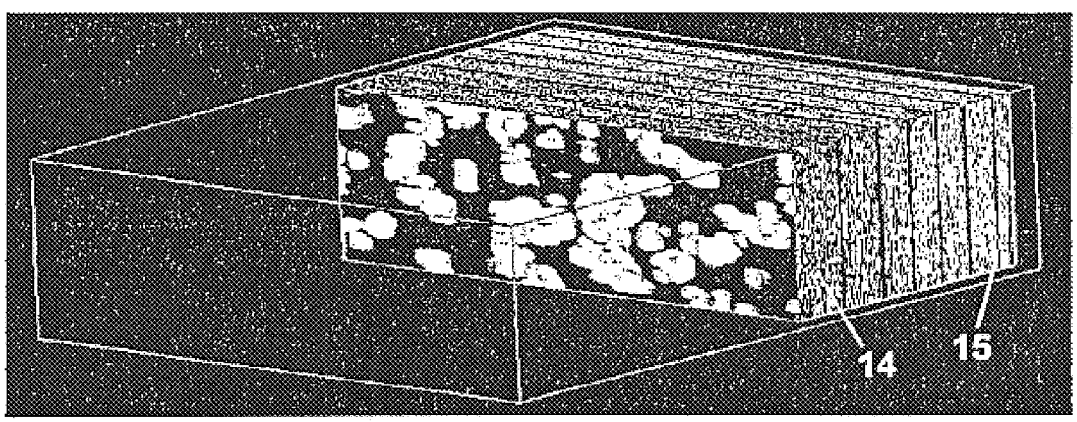
Figure 8C:
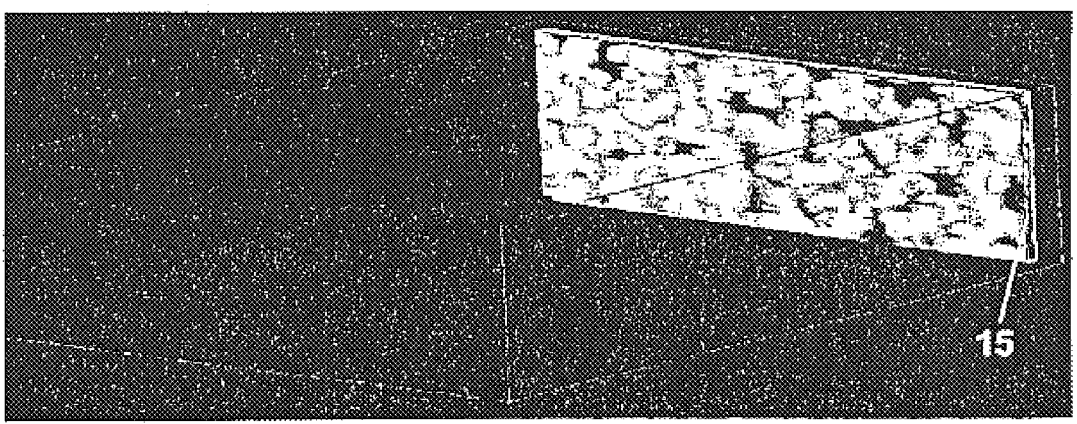

To separate colored noise signals from SAE signals, first a threshold value of 40 was defined for the color values before the evaluation of the 3D-data record. Only the "segmented color values" (40–255) that then remain above this threshold value were used for evaluation. FIG. 8 shows the 3D-view of the scanned agar phantom, as it was generated from the 3D-data record in Quanticon. Both the pixel number of the gray values and the pixel number of the segmented color values of all images of the data record were exported and further processed with MS-Excel® (Microsoft).

Figure 9:
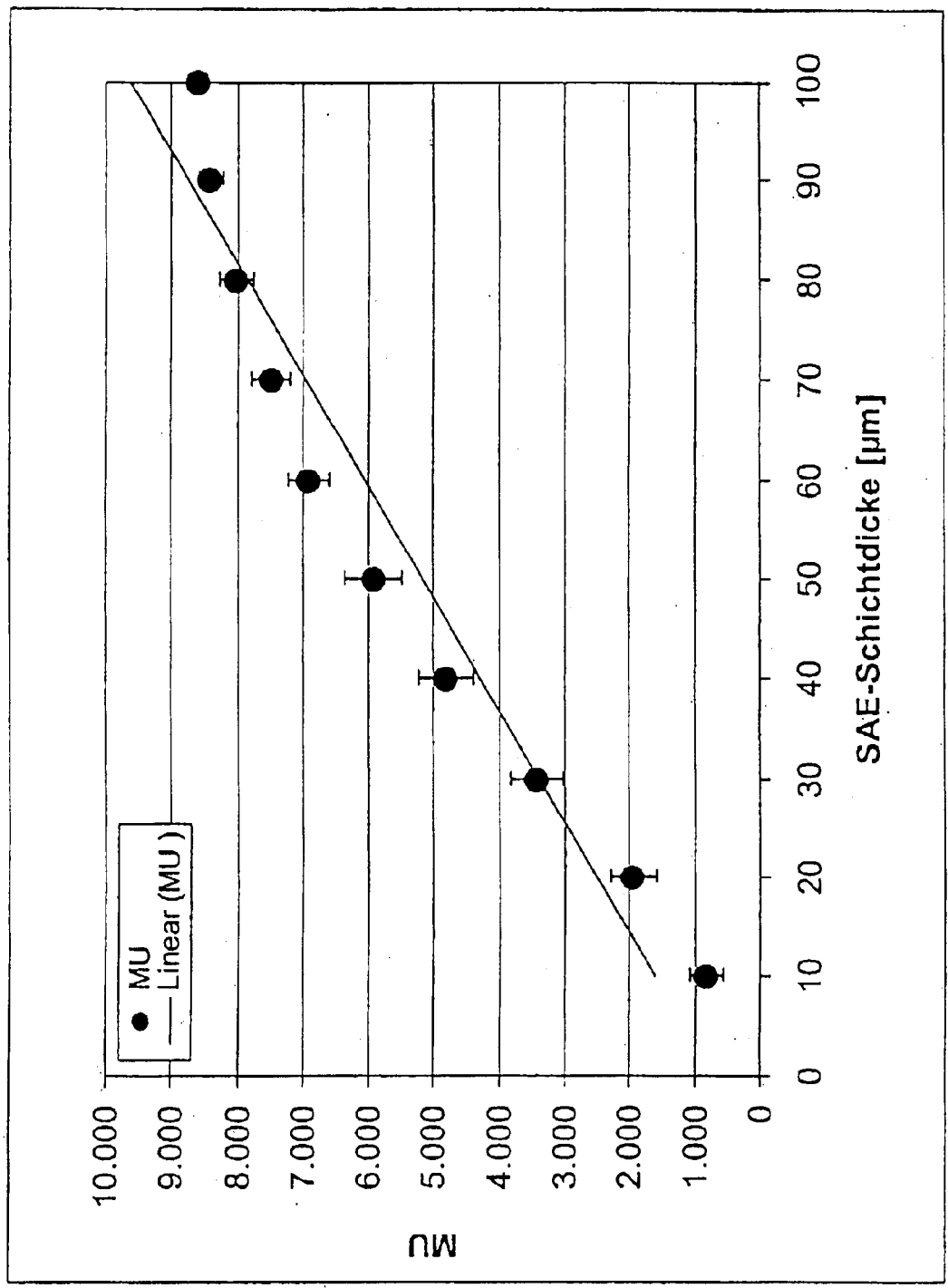

The diagram made in MS-Excel® of the segmented color values (MU) is shown in FIG. 9 based on the SAE layer thickness. Corresponding to the correction formula that is defined under "corrected MU," each individual color value was corrected. The resulting dependence on the SAE layer thickness is shown in FIG. 10 ($MUC_{corr.}$).

To convert the sum of the segmented color values into individual SAE signals or individual bubbles, first calculation factor $F_{sae}$ was determined. To this end, first the sum of the SAE signals was determined in 20 cross-sectional images by counting by hand. Then, the sum of the segmented color pixels was divided by the sum of the SAE effects that are counted by hand in the corresponding images. A mean value of 44 color pixels per SAE signal was determined. The diagram that is converted by this factor of $MU_{corr.}$ to the number of corrected SAE signals ($SAE_{corr.}$) is shown in FIG. 11.

Figure 10:
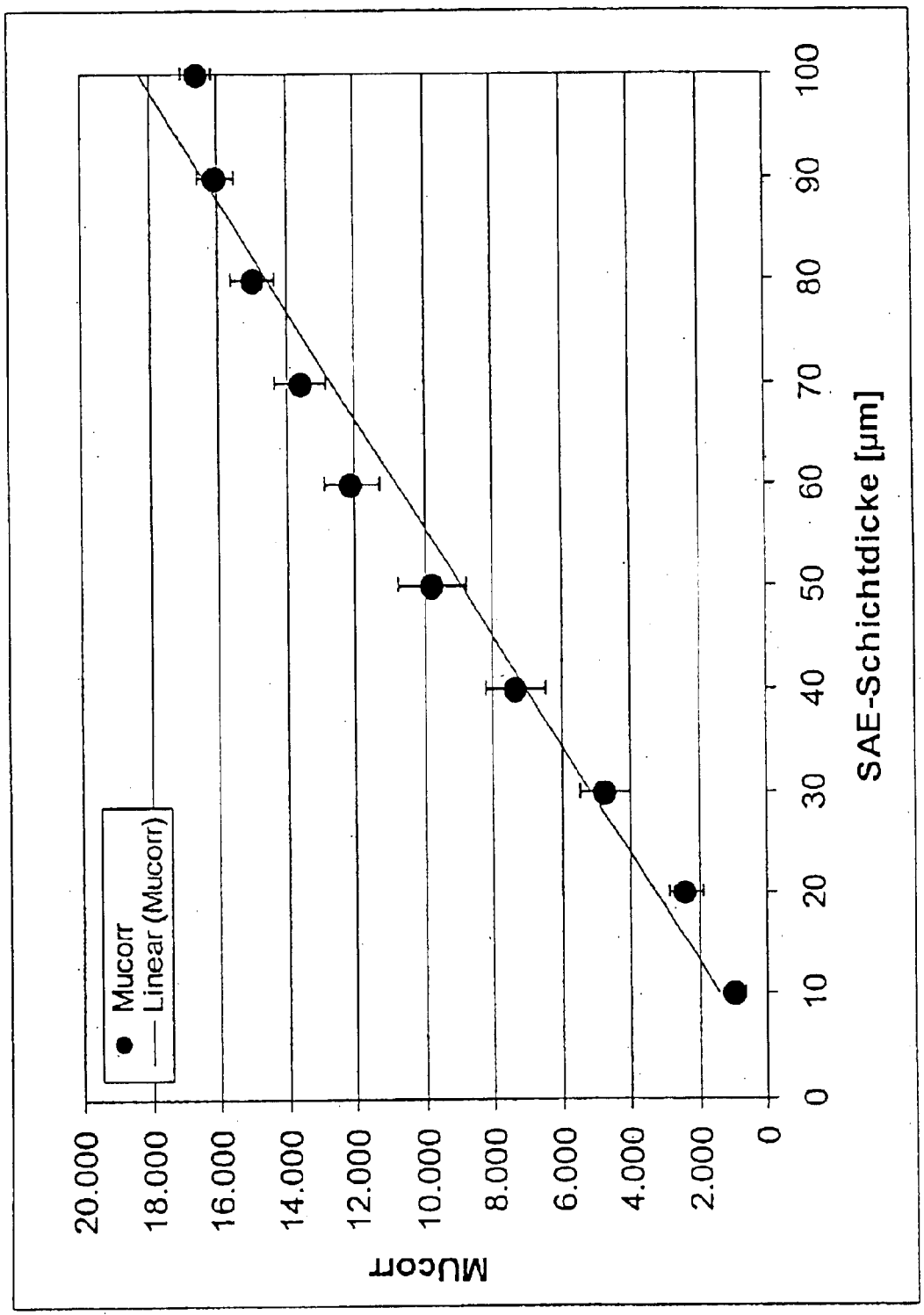
Figure 11:
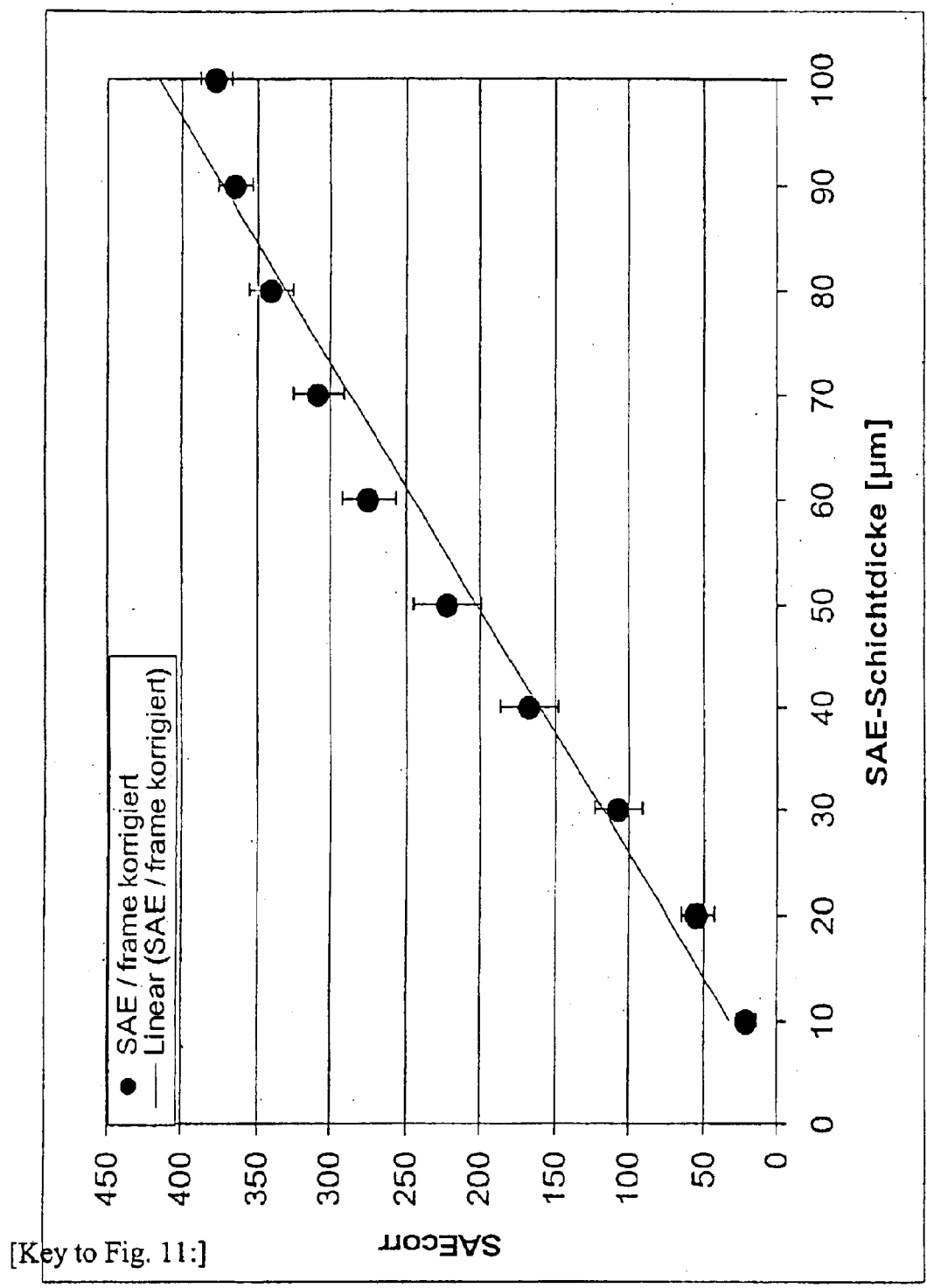

Table 1 lists the data on which FIGS. 9 to 11 are based:

TABLE 1

| | SAE Layer Thickness [μm/frame] | | | | | | | | | |
|---|---|---|---|---|---|---|---|---|---|---|
| | 10 | 20 | 30 | 40 | 50 | 60 | 70 | 80 | 90 | 100 |
| Color Saturation [%] | 9 | 21 | 37 | 52 | 64 | 75 | 81 | 87 | 91 | 93 |
| MU | 828 | 1.944 | 3.433 | 4.813 | 5.934 | 6.904 | 7.489 | 8.015 | 8.402 | 8.591 |
| ± | 260 | 345 | 402 | 430 | 441 | 316 | 292 | 243 | 183 | 158 |
| $Mu_{corr.}$ | 909 | 2.366 | 4.728 | 7.343 | 9.771 | 12.081 | 13.577 | 14.982 | 16.055 | 16.591 |
| ± | 309 | 492 | 706 | 876 | 1.004 | 787 | 763 | 663 | 517 | 451 |
| SAE/frame | 19 | 44 | 78 | 109 | 135 | 157 | 170 | 182 | 191 | 195 |
| ± | 6 | 8 | 9 | 10 | 10 | 7 | 7 | 6 | 4 | 4 |
| $SAE_{corr.}$/frame | 21 | 54 | 107 | 167 | 222 | 275 | 309 | 341 | 365 | 377 |
| ± | 7 | 11 | 16 | 20 | 23 | 18 | 17 | 15 | 12 | 10 |
| Number of Bubbles/ml | 12.233 | 14.363 | 16.912 | 17.779 | 17.536 | 17.004 | 15.810 | 14.805 | 13.796 | 12.695 |
| ± | 3.844 | 2.549 | 1.982 | 1.589 | 1.304 | 777 | 617 | 450 | 301 | 234 |
| Number of $Bubbles_{corr.}$/ml | 13.438 | 17.483 | 23.291 | 27.128 | 28.877 | 29.753 | 28.662 | 27.674 | 26.361 | 24.516 |
| ± | 4.566 | 3.632 | 3.476 | 3.236 | 2.967 | 1.938 | 1.610 | 1.224 | 848 | 667 |

The curve area between 30 and 70 μm of SAE layer thickness (~37–81% color saturation) can be described with a linear correlation function. Correlation coefficients of 0.990 result for the uncorrected MU or 0.996 of the corrected MU/SAE.

If the points outside this area in the linear correlation are also taken into consideration, the correlation coefficients fall off to 0.971 for MU or 0.981 for the corrected MU/SAE.

(e) Results:

(a) All images that were produced with the phantom being shifted by hand and a distance of travel of about 1 mm/frame are completely saturated with SAE signals. The saturation bubble concentration is exceeded, and a quantification is impossible.

(b) In the automatic shifting with overlapping of the sound fields, only individual SAE signals were detected with a shift of 10 μm/frame (FIG. 8). With increasing speed, the number of SAE signals/frame also increased. Only starting at a shift of 100 μm/frame did a color saturation in the image result.

Thus, a bubble concentration of 30,000 bubbles/ml with a layer thickness of 100 μm results in an SAE saturation. From this, a saturation bubble concentration of about 3,000 bubbles/ml can be concluded for a layer thickness of 1 mm.

(f) Discussion:

In contrast to commonly used scanning processes, a bubble quantification itself at bubble concentrations of greater than 3,000 bubbles/ml is possible by the process according to the invention.

By the defined overlapping shift of an object from the transducer, in each cross-sectional image only the newly added bubbles from the non-overlapping volumes are detected. The SAE layer thickness in the respective distance of travel per image can thus be reduced. The saturation bubble concentration is increased at the ratio in which the actual layer thickness of the sound field stands for distance of travel or for SAE layer thickness. A 10 μm shift from image to image simultaneously increases the spatial resolution and the saturation bubble concentration by a factor of 100 at a layer thickness of the sound field of 1 mm.

EXAMPLE 2

Ex-Vivo Quantification of Unspecifically Concentrated Bubbles in the Liver of Rats (a) Production of Bubbles:

The bubbles were produced according to Example 4(a).

(b) Examination:

Two rats (Wistar SCHOE, 220 g, female) were examined. Various doses of the bubble suspension that was produced according to a) were injected i.v. in the rats via the caudal vein. For rat 1, a dilution to $1*10^8$ bubbles/ml was produced, and for rat 2, a dilution to $1*10^7$ bubbles/ml in 0.9% NaCl solution that contains 0.02% Triton X 100 was produced.

Rat 1: $1*10^8$ bubbles/kg ($1*10^8$ bubbles/ml, 220 µl i.v.)

Rat 2: $1*10^7$ bubbles/kg ($1*10^7$ bubbles/ml, 220 µl i.v.)

30 minutes after injection, the rats were sacrificed by i.p. injection of 1 ml of a 1:1 volume mixture that consists of Rompun® 2% (20 mg of xylazine/ml) and Ketavet® 100 mg/ml (100 mg of ketamine base/ml):

The right lobe of the liver was removed in each case and put into a vessel that was filled with 0.9% (m/m) sodium chloride solution.

The vessels with the lobes of the liver were:

1. shifted by hand in the crosswise direction under the transducer at a speed of about 2 cm/s, which corresponded to a distance of travel of about 1 mm/frame, or
2. set on a servomotor (Limes 150, OWIS GmbH, Motor controller DC 500) and automatically moved past at varying speeds under the fixed transducer; the speeds were selected in such a way that by taking into consideration the given image rate of the ultrasonic device of 5.8 images/second and continuous motion of the vessel, the following distances of travel per image resulted:

Rat 1 ($1*10^8$ bubbles/kg): 15, 20, 30 µm/frame

Rat 2 ($1*10^7$ bubbles/kg): 20, 40, 80, 120 µm/frame

The ultrasound study was carried out analogously to Example 1 with the same device settings. The liver was moved past at a distance of 2 cm on the transducer. For all measurements, the same ROI was used. The value of the ROI (about 2 mm*6 mm, measured on the scale of the ultrasonic device) was selected in such a way that in all evaluated images, the ROI lay completely in the area of the liver tissue. In all measurements, the same enlargement was selected in Quanticon®.

To determine the ratio of the screen pixel to the object length [mm], a quadratic ROI of 2 mm edge length (determined based on the lengthwise measuring scale shown in the ultrasonic image) was measured in the ultrasonic image. To this end, the image was correspondingly enlarged with the zoom function that is present in Quanticon®. The sum of pixels in this ROI (MU) was 225. From this could be calculated a ratio of EINBETTEN 56.25 pixels/mm² (225/4). Finally, the bubble concentration/ml of liver was calculated via the measured volume (surface area of the ROI× distance of travel/frame). To convert the raw data (FP, GP, and S) in bubble concentration C in the tissue, the following formula was used:

$$C = 1000 \times \left( \frac{\sum FP \times \left(1 + \frac{\sum FP}{\sum FP + \sum GP}\right)}{F_{sae} \times S \times \frac{\sum GP + \sum FP}{Ff}} \right)$$

C: Bubble concentration in [bubbles/ml] or [$SAE_{corr.}$/ml]

S: SAE layer thickness or the shift between two images in [mm]

FP: Screen pixels that lie inside measurement window (ROI) in the area of the SAE effects that are shown.

GP: Screen pixels that lie inside measurement window (ROI) outside of the SAE effects that are shown.

Σsae: Sum of the SAE signals depicted in an ultrasonic image $$F_{sae}: \frac{\sum FP}{\sum sae}$$

$F_r$: Sum of all screen pixels in a mm² (measured based on the lengthwise scale that is indicated in the ultrasonic image)

(c) Results:

Table 2 compares and contrasts the bubble concentrations of rats. In addition, Table 2 contains the mean values of the percentage color saturation in the case of the respective SAE layer thickness.

TABLE 2

| | SAE Layer Thickness [µm/frame] | | | |
|---|---|---|---|---|
| Rat 1 | | | | |
| $1 * 10^8$/kg | 15 | 20 | 30 | |
| Bubble Concentration | 43.288 ± 17.381 | 54.267 ± 16.371 | 60.498 ± 10.113 | |
| [Bubbles/ml] | (n = 88) | (n = 127) | (n = 88) | |
| Color Saturation [%] | 33 | 49 | 72 | |
| Rat 2 | | | | |
| $1 * 10^7$/kg | 20 | 40 | 80 | 120 |
| Bubble Concentration | 2.557 ± 4.581 | 5.791 ± 6.355 | 14.826 ± 4.410 | 15.562 ± 1.881 |
| [Bubbles/ml] | (n = 71) | (n = 80) | (n = 53) | (n = 42) |
| Color Saturation [%] | 3 | 13 | 53 | 74 |

Figure 12A:
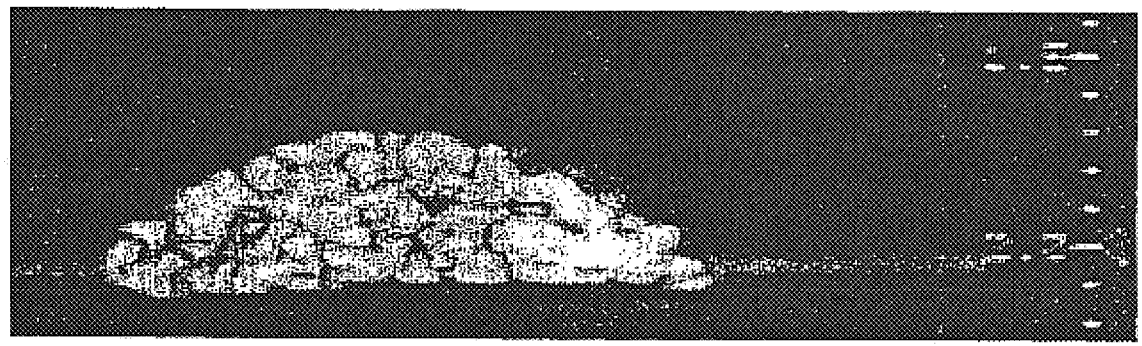
Figure 12B:
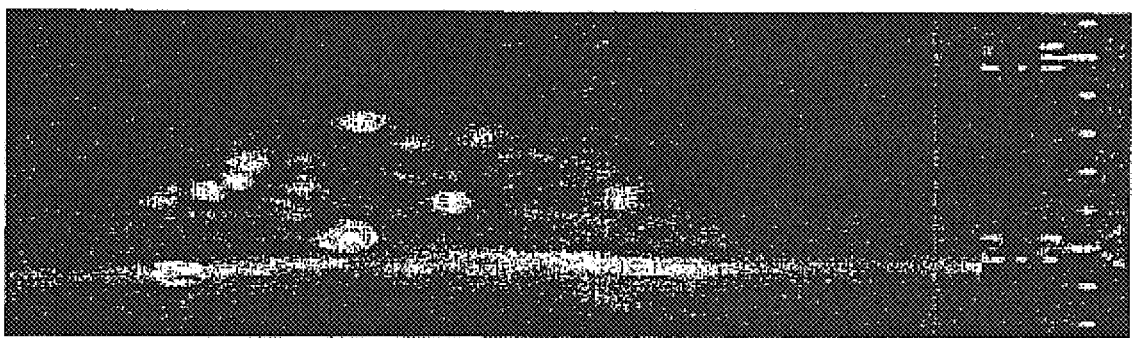
Figure 13A:
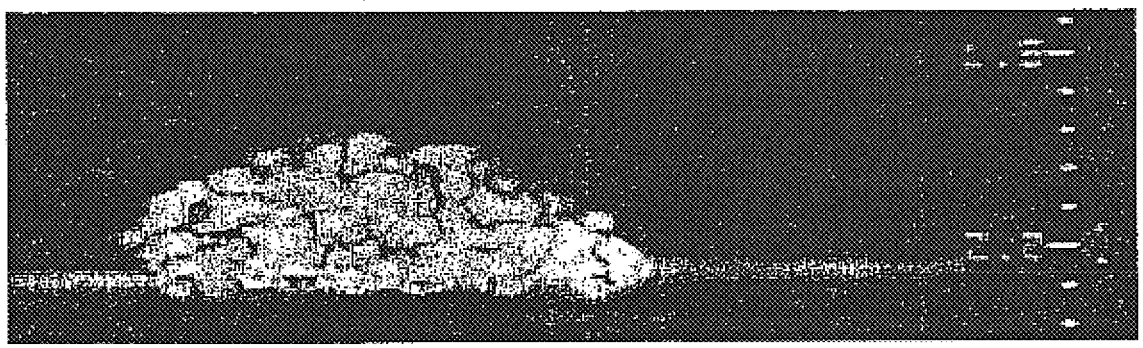
Figure 13B:
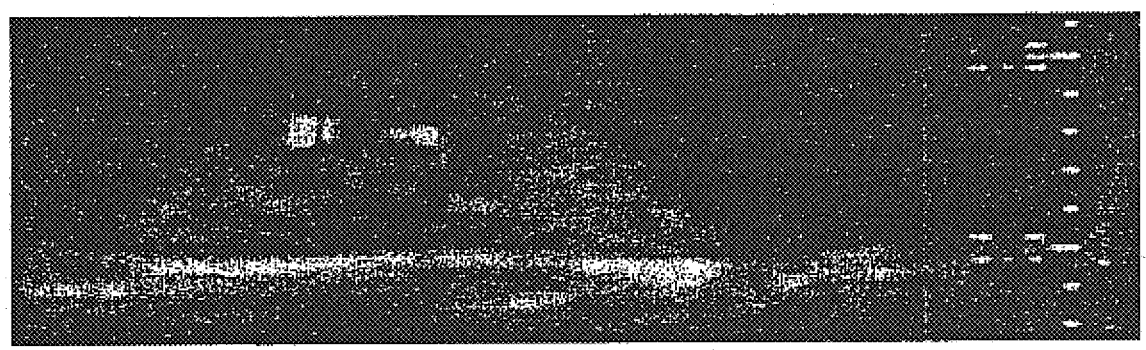

1. All images that are produced with the liver being shifted by hand and a distance of travel of about 1 mm/frame were completely saturated with SAE signals (FIG. 12*a*, FIG. 13*a*). The saturation bubble concentration was exceeded, and a quantification was impossible.
2. In the automatic shifting with overlapping of the sound fields, SAE signals in a quantifiable number were detected in rat 1 (dose: $1*10^8$ bubbles/kg) at SAE layer thicknesses of 20 to 120 µm/frame (FIG. 12*b*: SAE layer thickness: 20 µm), and in rat 2 (dose: $1*10^7$ bubbles/g) at SAE layer thicknesses of 10 to 30 µm/frame (FIG. 13*b*: SAE layer thickness: 20 µm). At increasing speed, the number of SAE signals/frame also increased.

Figure 14:
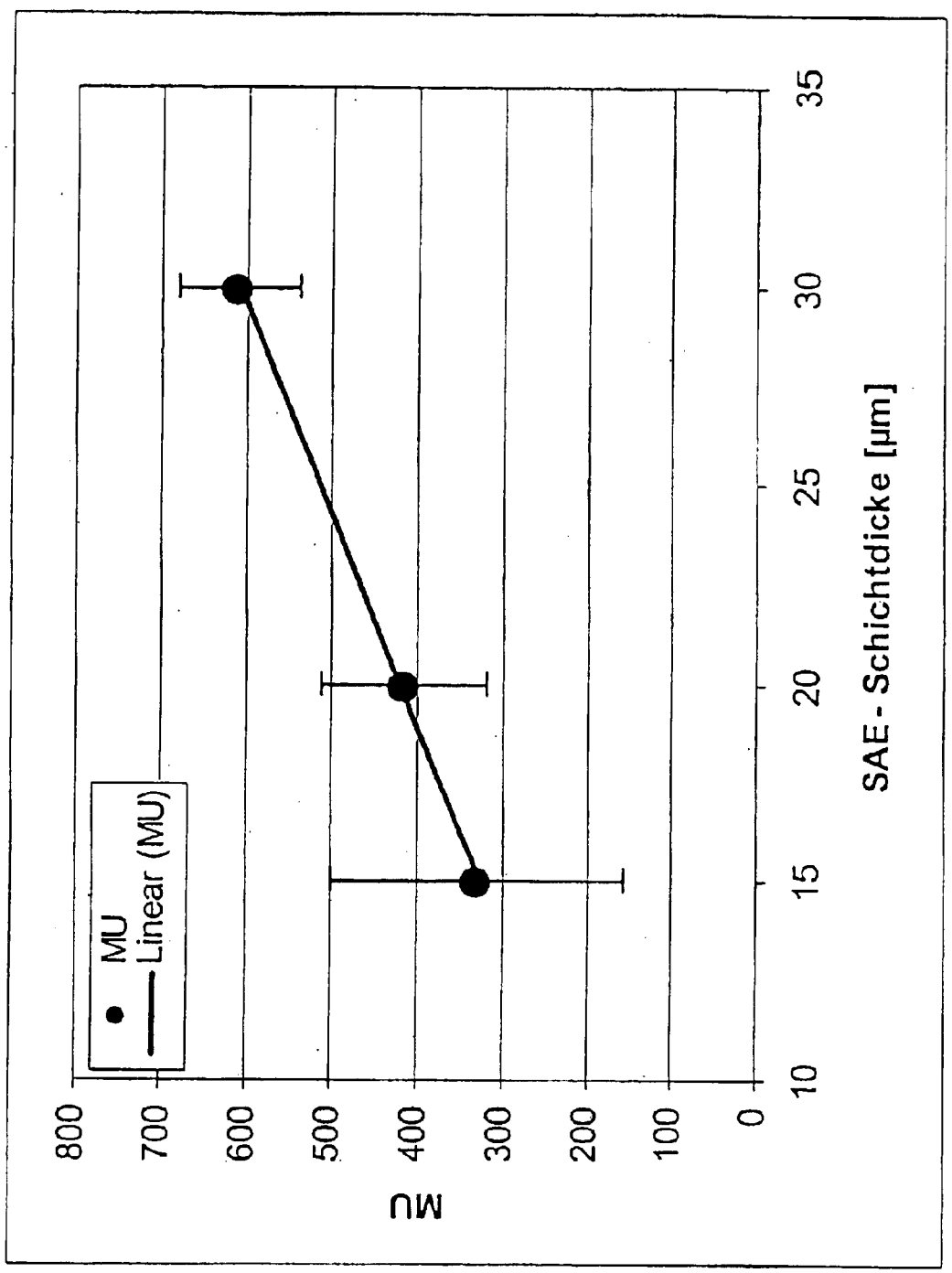
Figure 15:
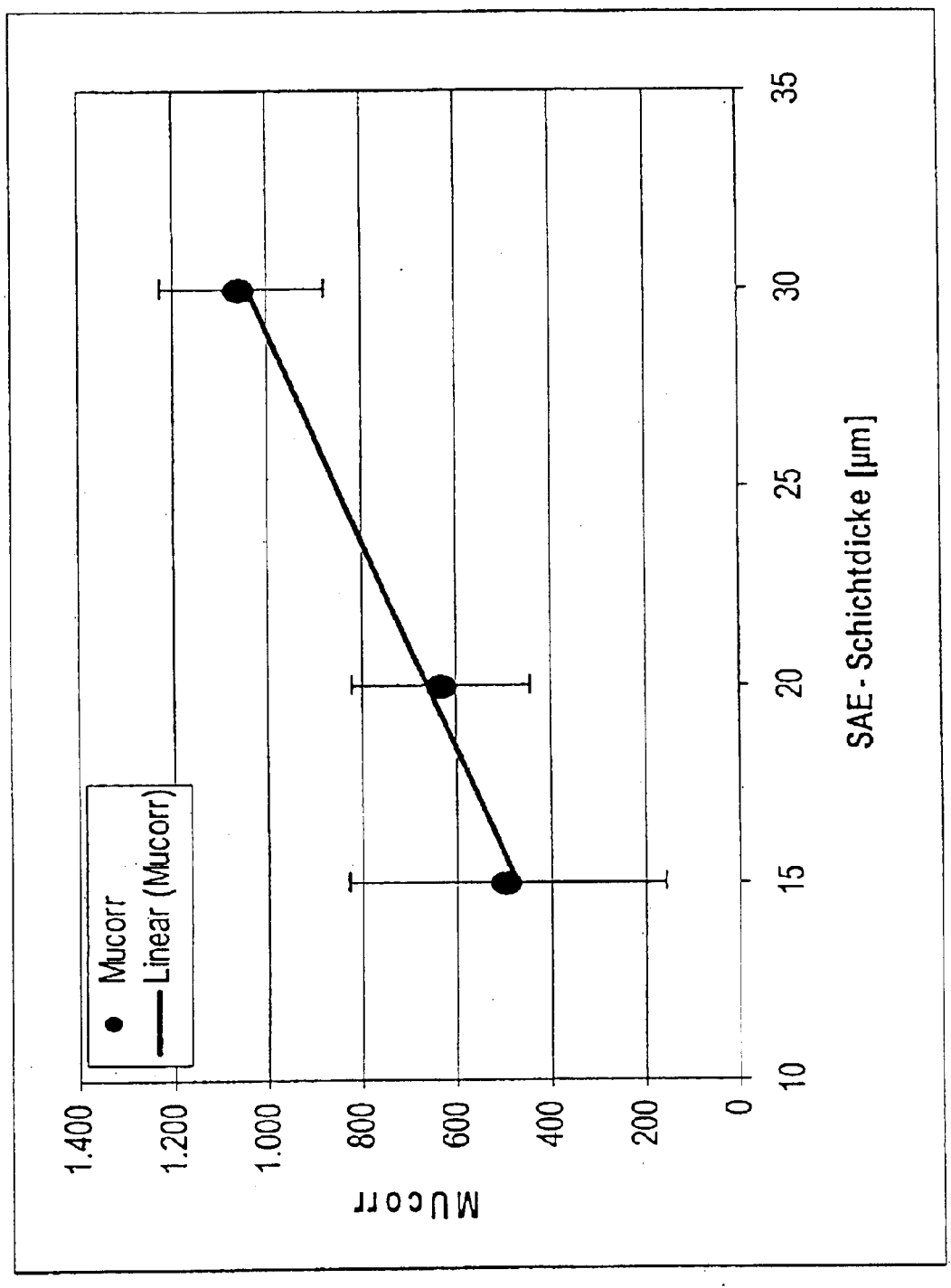
FIG. 15 shows dependence of $MU_{corr}$ on the SAE layer thickness
Rat 1 (Example 2): $1*10^8$ bubbles/ml; ex-vivo measurement, 30 minutes.
Figure 16:
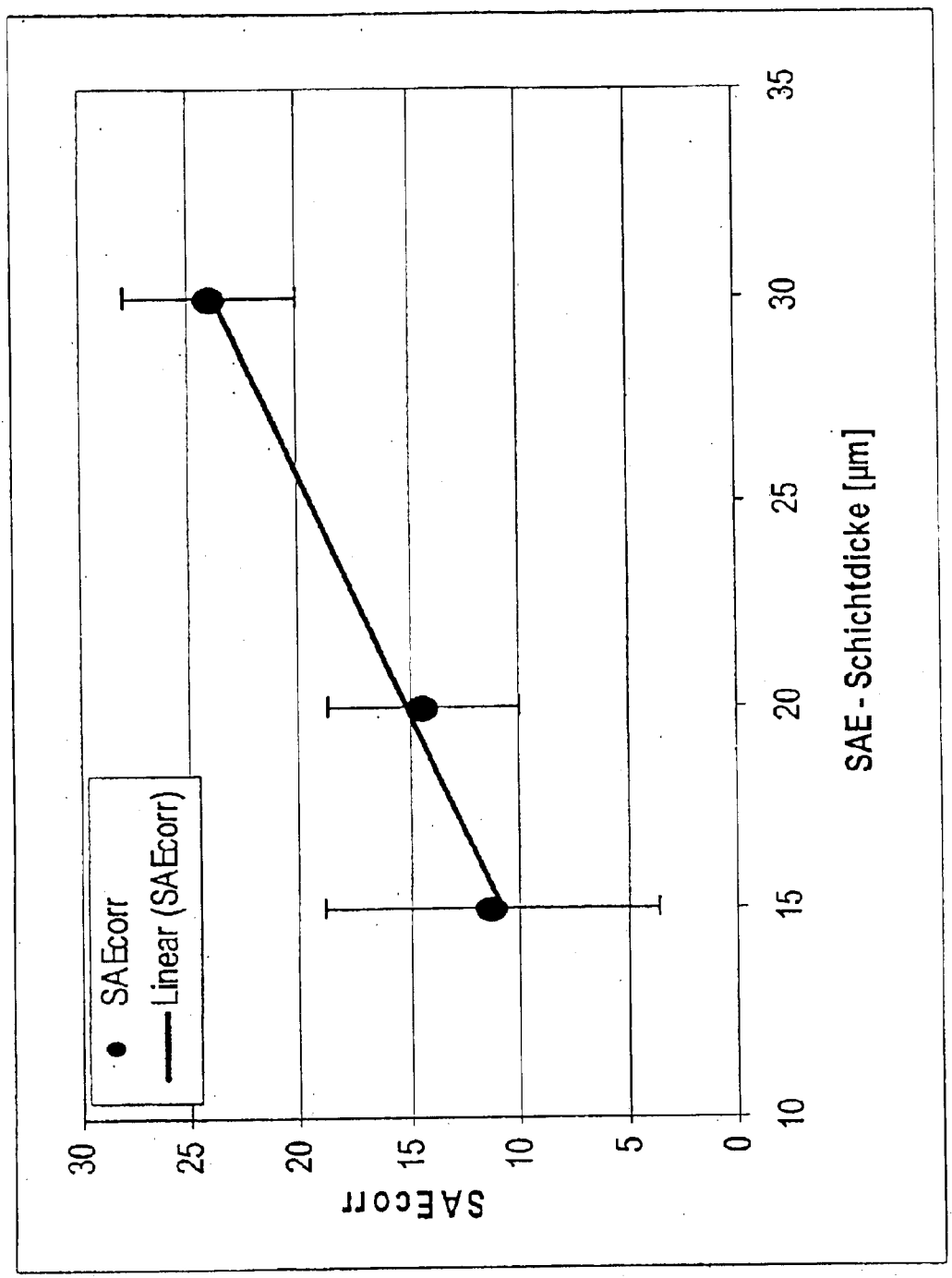
FIG. 16 shows dependence of $SAE_{corr}$ on the SAE layer thickness
Rat 1 (Example 2): $1*10^8$ bubbles/ml; ex-vivo measurement, 30 minutes.

3. In the case of rat 1, a linear correlation coefficient of 1,000 was calculated for the dependence of the uncorrected MU on the SAE layer thickness (FIG. 14). The linear correlation coefficient of the dependence of the corrected MU ($MU_{corr.}$) or corrected SAE ($SAE_{corr.}$) on the SAE layer thickness between 15 $\mu$m and 30 $\mu$m was preferably approximately 0.995 (FIGS. 15 and 16).

Figure 17:
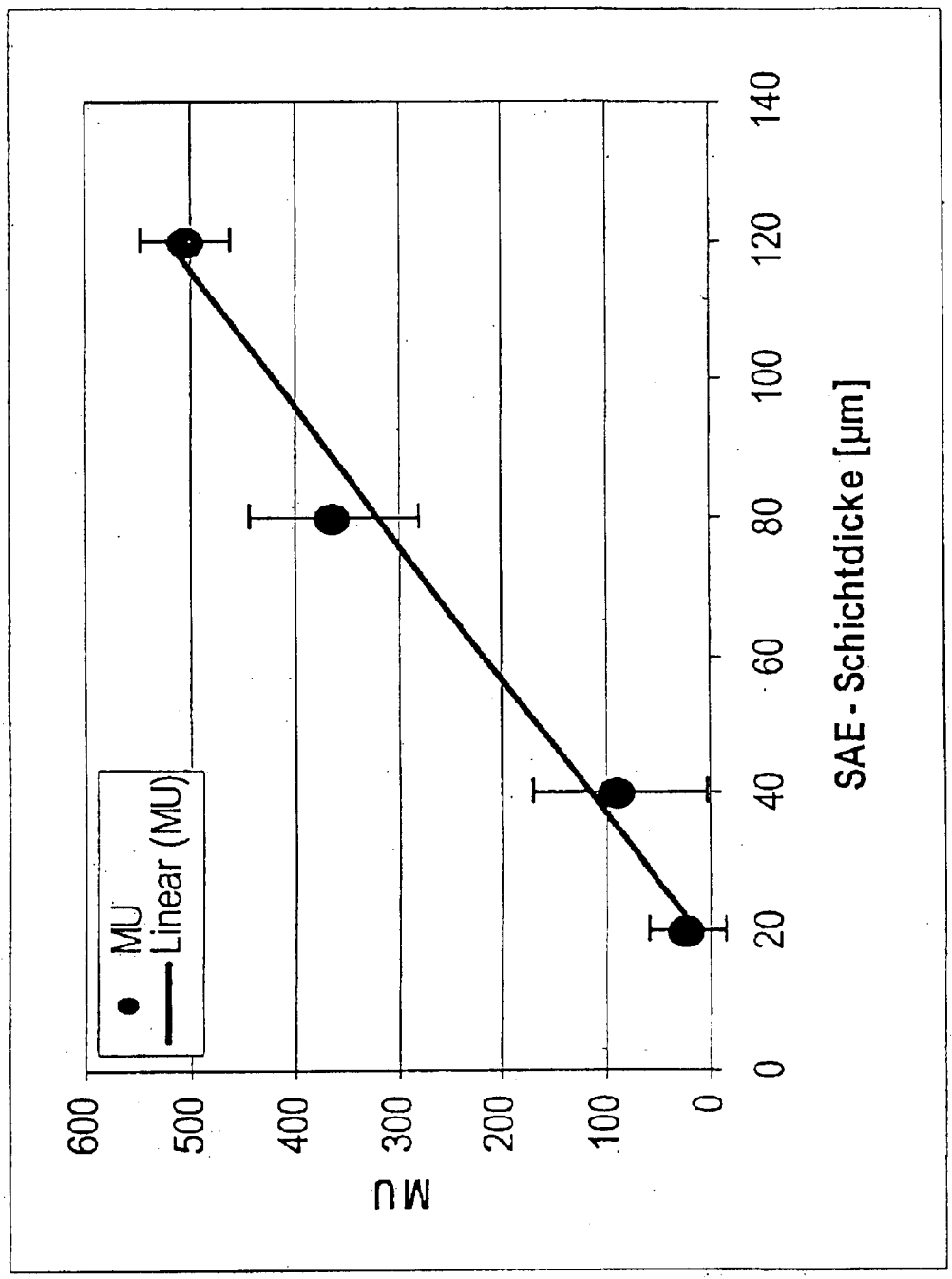
FIG. 17 shows dependence of MU on the SAE layer thickness
Rat 2 (Example 2): $1*10^7$ bubbles/ml; ex-vivo measurement, 30 minutes.
Figure 18:
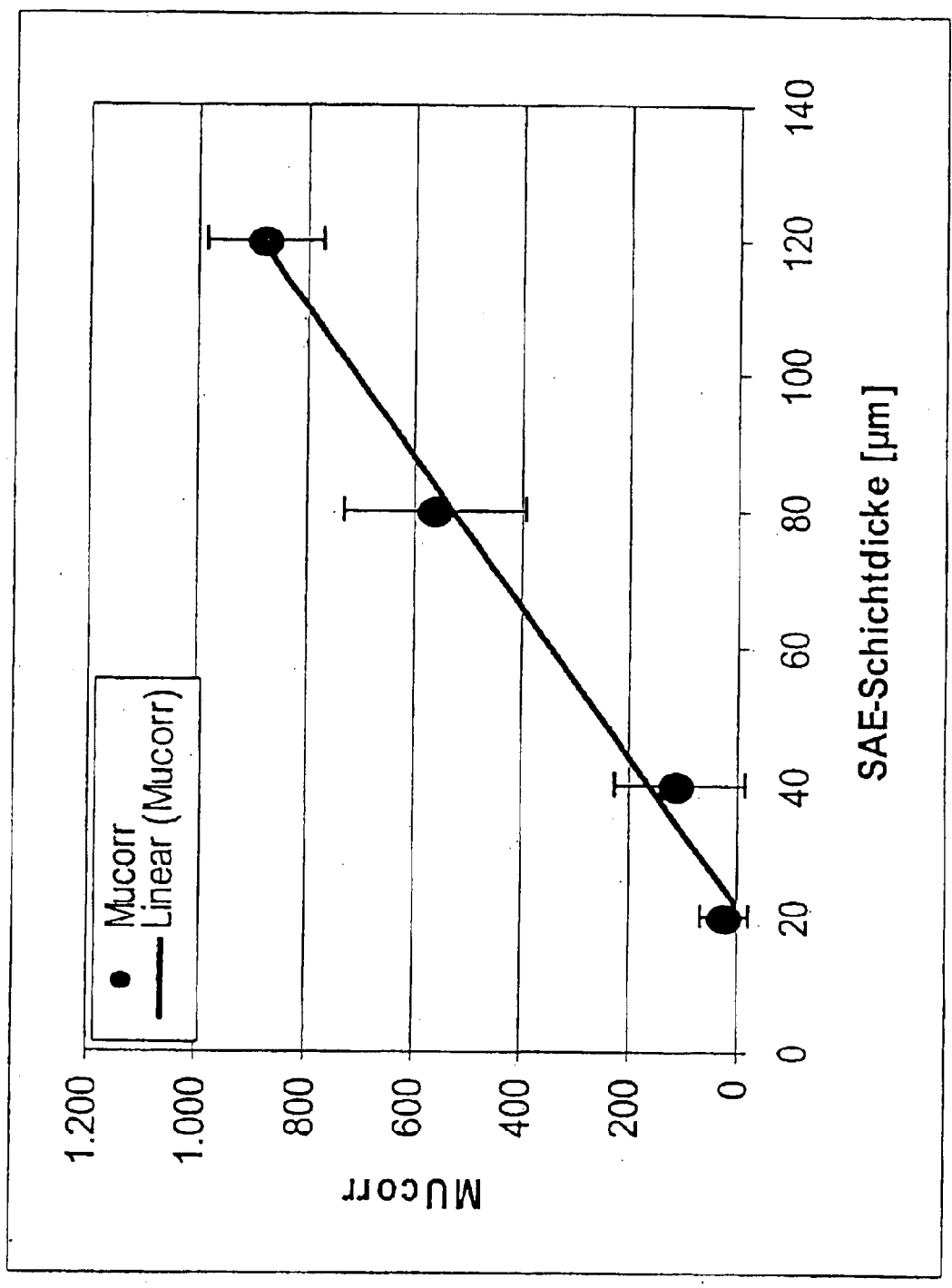
FIG. 18 shows dependence of $MU_{corr}$ on the SAE layer thickness
Rat 2 (Example 2): $1*10^7$ bubbles/ml; ex-vivo measurement, 30 minutes.
Figure 19:
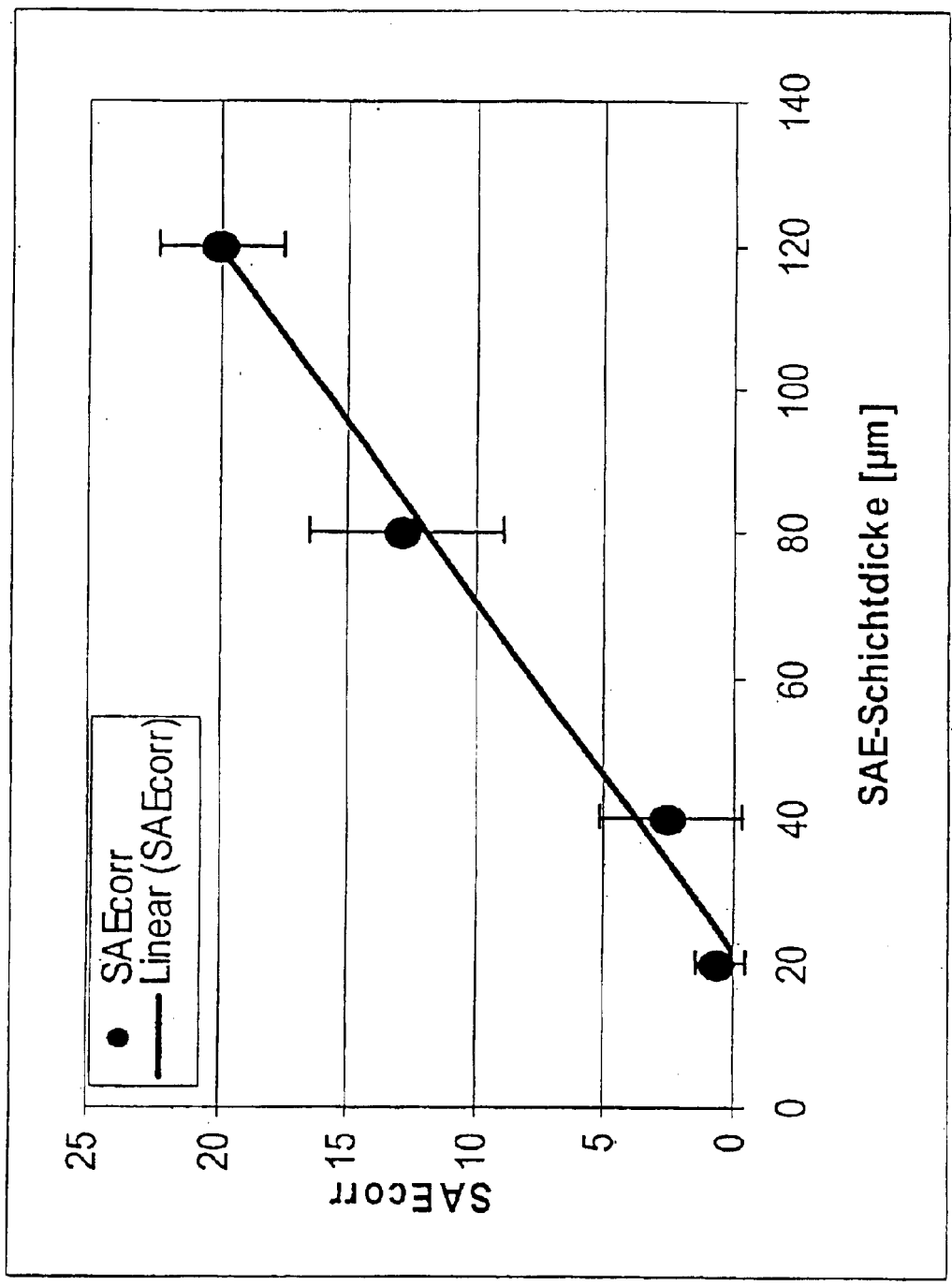
FIG. 19 shows dependence of $SAE_{corr}$ on the SAE layer thickness
Rat 2 (Example 2): $1*10^7$ bubbles/ml; ex-vivo measurement, 30 minutes.

4. In rat 2, a linear correlation coefficient of 0.984 was calculated for the dependence of the uncorrected MU on the SAE layer thickness (FIG. 17). The linear correlation coefficient for the dependence of the corrected MU ($MU_{corr.}$) or corrected SAE ($SAE_{corr.}$) on the SAE layer thickness between 20 $\mu$m and 120 $\mu$m was in each case approximately 0.995 (FIGS. 18 and 19).

5. The bubble number is in a linear ratio to the SAE layer thickness.

(d) Discussion:

The process according to the invention can also be used in organs that are removed, in which bubbles accumulate unspecifically. There is a narrow correlation between the number of SAE signals shown in the cross-sectional image and the corresponding SAE layer thickness. The bubble concentration in the livers of rats under examination is clearly distinguished based on the dose that is administered.

EXAMPLE 3

In-Vivo Quantification of Specifically Concentrated USKM in the F9-Ter Atom of the Mouse With the process according to Example 1, the accumulation of specific bubbles, to whose surface anti-CD105-antibodies were coupled, was examined in tumors of F9-tumor-carrying mice (Swiss nude) after i.v. injection in vivo. As a control substance, bubbles were used to whose surface IgG2a-antibodies (isotype control) were coupled.

(a) Production of Specific Bubbles:

The specific bubbles were produced and characterized according to Examples 4(a) to 4(e). The antibody coupling was carried out according to Example 4(f).

(b) Production of the Isotype Control:

The isotype-control bubbles were produced and characterized according to Examples 4(a) to (e). The isotype coupling was carried out according to Example 4(g).

(c) Tumor Inoculation:

F9-Tumor cells that were grown subconfluently in culture were trypsinized, centrifuged and resuspended in PBS with $Ca^{2+}/Mg^{2+}$. After staining with trypan blue and calculation of the cell concentration, the cell suspension was set at a concentration of $6*10^7$ cells/ml. The cell suspension was cooled on ice until it was used. Ten female nude mice (Swiss nude, 18–20 g of body weight) were subcutaneously inoculated by this cell suspension with 50 $\mu$l each per animal (=$3*10^6$ cells/animal) by means of a Hamilton syringe and 27G canula in the left flank region. The growth of the tumors (length and width) was controlled by measurement with a slide rule, and the volume of the tumor was determined approximately according to the following formula:

$$L \times B^2/2$$

L: Length [mm]
B: Width [mm]

The animals were examined 12 to 14 days after tumor inoculation. In this examination, the tumor sizes at this time were between 230 and 1600 mm$^3$.

(d) Application of the Specific Bubbles and the Isotype Control:

An ultrasonic contrast medium that contains specific bubbles (produced and characterized according to Examples 4(a) to (e) and antibody coupling according to Example 4(f)) in the waxy state was injected i.v. in a dose of $1*10^6$ bubbles/kg of body weight (corresponded to 200 $\mu$l of the suspension according to Example 4(g) for each 20 g mouse) into four mice. The specific bubbles were gas-filled microcapsules whose shells consisted of functionalized polybutylcyanoacrylate, and anti-CD105-antibodies were coupled to their surfaces. As a control substance, four additional mice were injected in the same way with an ultrasonic contrast medium that contains unspecific bubbles (produced and characterized according to Examples 4(a) to (e) and isotype coupling according to Example 4(g)). The unspecific bubbles were gas-filled microcapsules, whose shell also consisted of functionalized polybutylcyanoacrylate, but $IgG_{2a}$ (isotype control) was coupled to their surfaces.

The tumors of all animals were examined 60 minutes after administration of the respective ultrasonic contrast medium with respect to the degree of concentration with the process according to Example 1.

(e) Ultrasonic Examination:

For the examination, the mice were anesthetized with a 1:1 volume mixture that consists of a dilution (1+9) of Rompun® 2% (20 mg of xylazine/ml) and a dilution (1+4) of 100 mg/ml of Ketavet® (100 mg of ketamine base/ml) in physiological NaCl solution in each case. From this anesthetic mixture, 200 $\mu$l each per 20 g of mouse was injected i.p.

The mouse was fastened with adhesive strips to a carrier that was attached to the movable portion of a servomotor (Limes 150, OWIS GmbH, Motor controller DC 500). The servomotor was adjusted vertically with a support stand in such a way that the carrier with the mouse extended into a water basin (cut-to-length, square plastic flask). Before each scan, the basin was filled with fresh water that was tempered to 37° C. A transducer (L 10-5, ATL UM9) was provided with coupling gel and superposed with a support stand horizontal to the side wall of the water basin. While being monitored visually and sonographically, the mouse was moved into the basin to a point just short of where the tumor appears in the sound field. If air bubbles were to adhere to the skin, the latter were removed by carefully stretching a round, bent wire that had been coated with liquid soap over the skin. Then, the mouse was pulled back several millimeters. Before the scan, the necessary device settings were set on the ultrasonic device (color Doppler mode, MI: 1.1, persistence: 0, priority: maximum, penetration depth: 3 cm, focus: 2 cm). The scan was run at a constant SAE layer thickness of 285 $\mu$m/frame. In this case, the tumor lay in the area of the focus. After the scan, the image was "frozen," so that the transducer did not transmit any signal. The mouse was pulled back to the starting position. The transducer was turned on again, and the animal was scanned again at the same device settings and the same SAE layer thickness. The second scan was required to identify color signals that were not caused by SAE signals and that were used as control values. Such signals could be produced by flowing blood or larger air bubbles.

In the anesthesia that was used here, the respiratory rate of the animal was generally low enough to be able to perform a scan of about 3 cm in the SAE layer thickness that was used here within a pause for breath without artifacts of movement (FIG. 20b). In the case of longer examination times (e.g., with smaller SAE layer thickness) or at higher respiratory rates, respiratory artifacts could be avoided as follows:

a) Fastening the animal on a plastic carrier with a recess of at least the size of the tumor, such that the tumor lay in the recess, b) Measurement of the respiratory movement of the animal (e.g., with wire-strain gauges, dynamic-pressure measuring processes, etc.) and use as a trigger signal for controlling both the ultrasonic device and the servomotor.

(f) Evaluation:

A cross-sectional image was generated in scanning direction (FIG. 20b), and the latter was overlaid on the corresponding diagram of the measured values (FIG. 20a) on the same scale. The sum of the colored screen pixels within the tumor was evaluated with Quanticon® (3D-Echotech). For evaluation, only the color signals that are in the tumor ($MU_{FP}$: 20) and not the gray signals ($MU_{GP}$: 21) were taken into consideration. Lines 16 and 17 that were drawn in in FIGS. 20a/b delimit the tumor area during the first scan. The area of the second scan is shown between lines 18–19.

Moreover, in detail: Reference number 20 means color signals ($MU_{FP}$); Reference number 21 means gray signals ($MU_{GP}$); reference number 22 means sum of $MU_{FP}$ and $MU_{GP}$ or the measured tissue volume.

Figure 21:
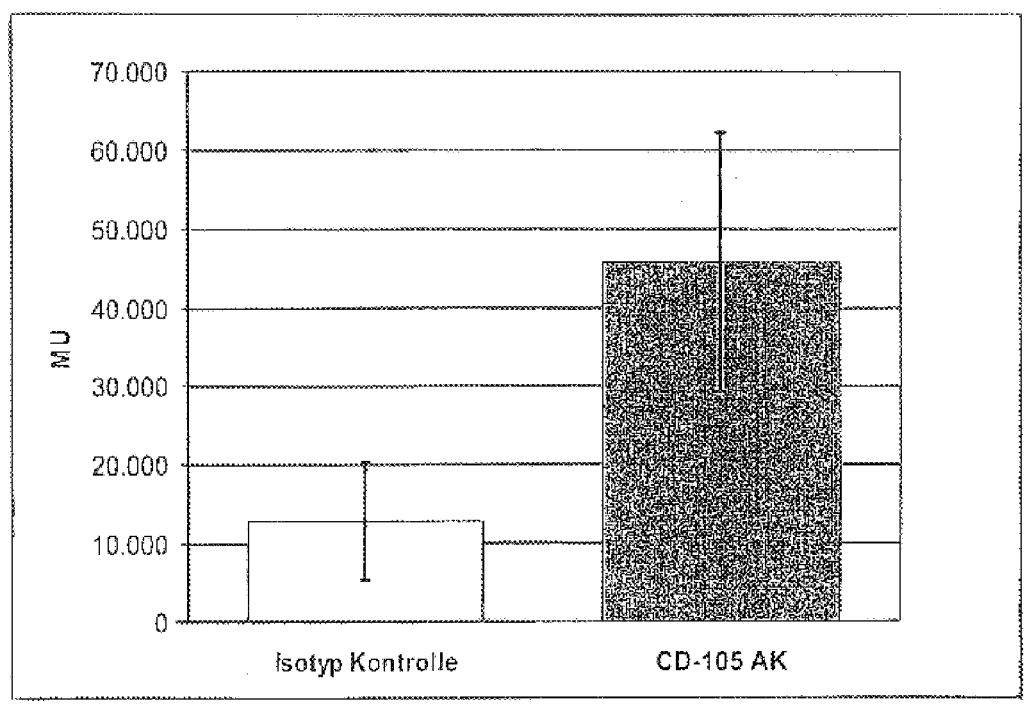

(g) Result:

For the isotype control, considerably fewer color signals (MU) were measured in the tumor (FIG. 21).

(h) Discussion:

The result shows that the process according to the invention is also suitable for quantifying specifically accumulated bubbles in the living organism. A significant difference can be detected with the process according to the invention itself when it is not scanned with maximum spatial resolution, and an SAE saturation results in some areas of some cross-sectional images. The number of signals in a specific bubble concentration can be distinguished from residual signals of the vascular system and/or signals of an unspecific bubble concentration.

EXAMPLE 4

Production of Ultrasonic Contrast Media (a) Production of the Microcapsule Suspension:

In a cylindrical steel reactor (inside dimensions: height=37 cm, diameter=29 cm), 7 l of an aqueous 1% (m/m) octoxynol solution was introduced at a pH of 2.5 and mixed with a mixer (dissolver disk: diameter=60 mm, stirring shaft: length=30 cm, immersion angle=10°) at high shear gradients (4000 rpm) and tempered (temperature of the solution=32° C.), so that a self-gassing (i.e., an introduction of air into the medium that is produced by the dispersion with strong foam formation) took place. 100 g of cyanoacrylic acid butyl ester was quickly added (<3 minutes) and dispersed (directly before the addition, the speed of rotation of the mixer was increased to 8,000 rpm). It was polymerized with self-gassing for 60 minutes, whereby gas-filled microcapsules (bubbles in terms of the definition on which the application is based) were formed. In a spherical separating funnel, the flotated material was separated for 3 days in the field of gravity of the earth, the subnatant was drained off, and the flotated material was resuspended with 3 l of an aqueous 0.02% (m/m) octoxynol solution. The thus obtained microcapsule suspension had a polymer content of 9.46 mg/ml, a density of 0.943 g/ml and a pH of 3.5.

(b) Particle Size and Particle Concentration of the Gas-Filled Microcapsules:

The particle size distribution of the microcapsule suspension according to Example 4 (a) was determined with a particle counter of the Particle Sizing Systems Company, AccuSizer 770 type (measurement medium: aqueous 0.02% (m/m) Triton X 100 solution). The volume-weighted particle size distribution extended from 0.8 to 10 μm with a maximum of 1.8 μm, and the microcapsule concentration was $7.2*10^9$ ($\pm 1*10^8$) particles per ml.

(c) Functionalization of the Gas-Filled Microcapsules by Partial Side-Chain Hydrolysis:

2500 g of a microcapsule suspension according to Example 4(a) was mixed while being stirred with 50 l g of sodium hydroxide solution with the concentration $8*10^{-2}$ mol/l. A pH of 12 was set in the reaction batch. It was stirred for 20 minutes at room temperature. Then, the pH was set at 3.5 with 1N hydrochloric acid.

(d) Particle Size and Particle Concentration of the Gas-Filled Microcapsules:

The particle size distribution of the microcapsule suspension according to Example 4(c) was determined with a particle counter of the Particle Sizing Systems Company, AccuSizer 770 type (measurement medium: aqueous 0.02% (m/m) Triton X 100 solution). The volume-weighted particle size distribution extended from 0.8 to 10 μm with a maximum at 1.8 μm, and the microcapsule concentration was $6.0*10^9$ ($\pm 1*10^8$) particles per ml.

(e) Binding of Streptavidin to Functionalized Gas-Filled Microcapsules:

The microcapsule suspension according to Example 4(c) was purified by flotation at least 5× from 0.02% (m/m) Triton-X100 solution (pH=4.5, set with hydrochloric acid). $7.5*10^8$ particles of the purified suspension were added with 15 ml of sodium acetate buffer in a scintillation vial and stirred by means of a stickel stirrer on a magnetic stirrer. (Sodium acetate buffer=solution A: 1.36 g of $NaCH_3COO*3 H_2O$, M=136.08 g/mol of Riedl-de Haen per 500 ml of water, solution B: 571 μl of glacial acetic acid, M=60.05 g/mol per 500 ml of water, 400 ml of solution A was introduced and set with solution B at a pH of 4.5).

300 μg of streptavidin (SIGMA Company) was dissolved in 300 μl of water that was sterilized by filtration. The solution was added to the sodium acetate buffer-microcapsule suspension. The pH should be 4.5±0.2. Then, 750 μg of EDC (1 ethyl-3-(3-dimethylaminopropyl) carbodiimide hydrochloride (SIGMA) was quickly dissolved in 750 μl of water that was sterilized by filtration and added to the buffer solution.

Stirring was then continued for one hour under intermittent pH control. It was further stirred overnight (about 17 hours) at 4° C.

In the end, a solution that consisted of 188 μl of 1 M ethanolamine solution (SIGMA) in 3.75 ml of water was added to the batch.

After flotation (24 hours), the batch was concentrated by evaporation by draining the subnatant to a volume of 1 ml. Then, 10 ml of Hepes buffer/0.01% (m/m) Triton solution (30 ml of 5 M NaCl solution+10 ml of 1 M Hepes solution (Gibco 15630-056) per 1000 ml of 0.01% (m/m) Triton solution, pH 7.4) was added thereto, floated again, and the subnatant was drained off again to a volume of 1 ml. The concentrated suspension was then moved into a siliconized Eppendorf reaction vessel and stored in a refrigerator.

The success of coupling was checked in the FACS (flow cytometer of the Becton Dickinson) with FITC-biotin. With the aid of a saturation series, 200,000 streptavidin molecules per microcapsule were thus quantified.

(f) Binding of Biotinylated Anti-CD105 Antibodies to Functionalized Gas-Filled Microbubbles:

The suspension of gas-filled microbubbles according to Examples 4(a) to (d), to which streptavidin had been bonded according to Example 4(e), was incubated for 10 minutes at room temperature with biotinylated anti-CD105-antibodies (rat anti-mouse CD105/endoglin, biotin conjugates, Southern Biotechnology Associates, Inc., Cat. No. 1860-08) at a ratio of 0.5 $\mu$g of antibodies to 1e6 microbubbles. After incubation, the suspension was diluted to 1e8 bubbles/ml with PBS buffer, containing 0.02% (m/m) Triton x 100. The CD105 coupling and dilution were freshly produced for each animal.

(g) Binding of Biotinylated $IgG_{2a}$ to Functionalized Gas-Filled Microcapsules:

The suspension of gas-filled microbubbles according to Examples 4(a) to (d), to which streptavidin had been bonded according to Example 4(e), was incubated for 10 minutes at room temperature with biotinylated $IgG_{2a}$ isotype control (rat $IgG_{2a}$ isotype control, biotin conjugates, Southern Biotechnology Associates, Inc., Cat. No. 0117-08) at a ratio of 0.5 $\mu$g of antibodies to 1e6 microbubbles.

After incubation, the suspension was diluted to 1e8 bubbles/ml with PBS buffer, containing 0.02% (m/m) Triton x 100. The isotype coupling and dilution was freshly produced for each animal.

The entire disclosures of all applications, patents and publications, cited herein and of corresponding German Patent Application No. 102 15 335.3, filed May 28, 2002, and U.S. Provisional Application Serial No. 60/378,358, filed May 8, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A device far quantification of bodies that are contained in an object under examination, comprising
    a) at least one transducer for emitting an ultrasound field with which the bodies that are contained in a layer in the object under examination can be excited to emit characteristic ultrasonic signals, and to receive characteristic signals,
    b) at least one data processing system to determine the number of bodies in the layer that consists of the characteristic signals, and
    c) means with which the ultrasound field can be shifted after an excitation of bodies in a first layer in an object under examination, such that bodies can be excited after shifting into a second layer, whereby the first layer and the second layer overlap and are displaced relative to one another in a parallel and defined manner.

2. A device according to claim 1, wherein the bodies are bubbles.

3. A device according to claim 1, wherein the ultrasound field can be shifted by at least 5 $\mu$m.

4. A device according to claims 1, wherein at least one transducer exhibits a two-dimensional or a three-dimensional array of piezo crystals.

5. A device according to claim 4, wherein means are provided with which the object under examination and the two-dimensional array are shifted relative to one another.

6. A device according to claim 4, wherein a control for the piezo crystals in the three-dimensional array is provided, with which adjacent sound fields emanating from piezo crystals in a piezo crystal row in the array or sound fields emanating from adjacent piezo crystal rows in the array can be overlapped.

7. A device according to claim 4, wherein means are provided with which the object under examination and at least one transducer are shifted relative to one another.

8. A device according to claim 1, wherein at least one motor drive is provided to shift the object under examination or at least one transducer relative to one another.

9. A device according to claim 1, wherein a holding device, with which the object under examination is clamped, and a movable holding device for at least one transducer are provided.

10. A device according to claim 1, wherein an image evaluation system for data processing and image display is provided with which the quantification of bodies can be implemented by video densitometry.

11. A device according to claim 10, wherein the bodies are bubbles.

12. A method for ultrasonic diagnosis and/or ultrasonic therapy in a human or in an animal, comprising quantifying bodies in the human or in the animal with a device according to claim 1.

13. A method for in-vivo and ex-vivo mapping of physiologically upward- or downward-adjustable molecular markers in an organ or a tissue starting from postembryonic ontogenesis, for in-vivo and ex-vivo mapping of pathologically upward- or downward-adjustable molecular markers in an organ or a tissue during pathogenesis, or for the characterization of cell cultures by in-vitro mapping of upward- and downward-adjustable molecular markers in a cells. Comprising quantifying bodies that have one or more specific binding molecules for the markers with a device according to claim 1.

14. A method according to claim 13, wherein the bodies are bubbles.

15. A process for quantification of bodies that are contained in an object under examination, comprising
    a) exciting bodies with an ultrasound field that are contained in a layer in the object under examination to produce characteristic ultrasonic signals,
    b) receiving the ultrasonic signals,
    c) determining the number of bodies from the ultrasonic signals that are received, and
    d) after bodies are excited in a first layer in the object under examination, shifting the ultrasound field such that bubbles are excited after displacement into a second layer, whereby the first layer and the second layer overlap and are shifted relative to one another in a parallel and defined manner.

16. A process according to claim 15, wherein the bodies are bubbles.

17. A process according to claim 16, wherein the bubbles are destroyed when excited and are excited to emit the characteristic signals.

18. A process according to claim 15, wherein the ultrasound field is shifted by at least 5 $\mu$m.

19. A process according to claim 15, wherein the object under examination and at least one transducer that emits the ultrasound field are shifted relative to one another.

20. A process according to claim 19, wherein the object under examination is shifted relative to at least one fixed transducer or wherein at least one transducer is shifted relative to a fixed object under examination.

21. A process according to claim 15, wherein the object under examination is a human, an animal, an organ, a tissue or a cell.

* * * * *